United States Patent
Dafna et al.

(10) Patent No.: US 11,712,198 B2
(45) Date of Patent: Aug. 1, 2023

(54) ESTIMATION OF SLEEP QUALITY PARAMETERS FROM WHOLE NIGHT AUDIO ANALYSIS

(71) Applicants: B.G. NEGEV TECHNOLOGIES AND APPLICATIONS LTD., AT BEN-GURION UNIVERSITY, Beer-Sheva (IL); MOR RESEARCH APPLICATIONS LTD., Tel Aviv (IL)

(72) Inventors: Eliran Dafna, Beer-Sheva (IL); Yaniv Zigel, Omer (IL); Dvir Ben Or, Gedera (IL); Matan Halevi, Givat Avni (IL); Ariel Tarasiuk, Meitar (IL)

(73) Assignees: B.G. NEGEV TECHNOLOGIES AND APPLICATIONS LTD., AT BEN-GURION UNIVERSITY, Beer-Sheva (IL); MOR RESEARCH APPLICATIONS LTD., Tel Aviv (IL)

( * ) Notice: Subject to any disclaimer, the term of this patent is extended or adjusted under 35 U.S.C. 154(b) by 1092 days.

(21) Appl. No.: 16/316,454

(22) PCT Filed: Jul. 11, 2017

(86) PCT No.: PCT/IL2017/050786
§ 371 (c)(1),
(2) Date: Jan. 9, 2019

(87) PCT Pub. No.: WO2018/011801
PCT Pub. Date: Jan. 18, 2018

(65) Prior Publication Data
US 2020/0093423 A1 Mar. 26, 2020

Related U.S. Application Data

(60) Provisional application No. 62/361,013, filed on Jul. 12, 2016, provisional application No. 62/360,487, filed on Jul. 11, 2016.

(51) Int. Cl.
*A61B 5/00* (2006.01)
*G16H 50/20* (2018.01)
(Continued)

(52) U.S. Cl.
CPC .......... *A61B 5/4815* (2013.01); *A61B 5/0816* (2013.01); *A61B 5/1118* (2013.01);
(Continued)

(58) Field of Classification Search
None
See application file for complete search history.

(56) References Cited

U.S. PATENT DOCUMENTS 6,003,003 A * 12/1999 Asghar .................. G10L 15/02
704/256.5
10,058,290 B1 * 8/2018 Proud .................... A61B 5/749
(Continued)

FOREIGN PATENT DOCUMENTS

WO WO 2006/066337 6/2006
WO WO 2012/025892 3/2012
(Continued)

OTHER PUBLICATIONS

International Search Report for PCT/IL2017/050786 dated Nov. 6, 2017.
(Continued)

*Primary Examiner* — Michael R Bloch
(74) *Attorney, Agent, or Firm* — Nixon & Vanderhye PC

(57) ABSTRACT

The present invention relates to a system and method for determining sleep quality parameters according to audio analyses, comprising: obtaining an audio recorded signal comprising sleep sounds of a subject; segmenting the signal into epochs; generating a feature vector for each epoch, wherein each of said feature vectors comprises one or more feature parameters that are associated with a particular characteristic of the signal and that are calculated according to the epoch signal or according to a signal generated from the epoch signal; inputting the generated feature vectors into a machine learning classifier and applying a preformed classifying model on the feature vectors that outputs a probabilities vector for each epoch, wherein each of the probabilities vectors comprises the probabilities of the epoch being each of the sleep quality parameters; inputting the probabilities vectors for each epoch into a machine learning time series model and applying a preformed sleep quality time series pattern function on said probabilities vectors that outputs an enhanced probabilities vector for each epoch;

(Continued)

determining a final sleep quality parameter for each epoch by calculating the most probable sleep quality parameters sequence.

21 Claims, 8 Drawing Sheets

(51) Int. Cl.
    *G06N 20/00*     (2019.01)
    *A61B 5/08*     (2006.01)
    *A61B 5/11*     (2006.01)
    *A61B 7/00*     (2006.01)
    *G06N 7/01*     (2023.01)

(52) U.S. Cl.
    CPC .......... *A61B 5/4812* (2013.01); *A61B 5/4818* (2013.01); *A61B 5/7207* (2013.01); *A61B 5/7264* (2013.01); *A61B 7/003* (2013.01); *G06N 7/01* (2023.01); *G06N 20/00* (2019.01); *G16H 50/20* (2018.01)

(56) References Cited

U.S. PATENT DOCUMENTS

| | | | | |
|---|---|---|---|---|
| 2009/0287107 | A1* | 11/2009 | Beck-Nielsen | A61B 5/369 600/544 |
| 2013/0184601 | A1* | 7/2013 | Zigel | A61B 5/4818 600/529 |
| 2015/0119741 | A1* | 4/2015 | Zigel | A61B 5/7275 600/529 |

FOREIGN PATENT DOCUMENTS

| | | |
|---|---|---|
| WO | WO 2013/106700 | 7/2013 |
| WO | WO 2013/179254 | 12/2013 |
| WO | WO 2014/115115 | 7/2014 |

OTHER PUBLICATIONS

Dafna et al., "Automatic Detection of Whole Night Snoring Events Using Non-Contact Microphone" *PloS one*, vol. 8, iss. 12: e84139, 14 pages (2013).

Dafna et al., "Sleep-Wake Evaluation from Whole-Night Non-Contact Audio Recordings of Breathing Sounds" *PloS one*, vol. 10, iss. 2: e0117382, 22 pages (2015).

Khandoker et al., "Automated Scoring of Obstructive Sleep Apnea and Hypopnea Events Using Short-Term Electrocardiogram Recordings" *IEEE Transactions on Information Technology in Biomedicine*, vol. 13, No. 6: 1057-1067 (2009).

Rosenwein et al., "Detection of Breathing Sounds During Sleep Using Non-Contact Audio Recordings" *Conf Proc IEEE Eng Med Biol Soc.*, 4 pages (2014).

Várady et al., "A Novel Method for the Detection of Apnea and Hypopnea Events in Respiration Signals" *IEEE Transaction on Biomedical Engineering*, vol. 49, No. 9: 936-942 (2002).

Yuichiro Anzai, "Pattern Recognition and Machine Learning," Academic Press, Inc., Jul. 1992, 412 pages.

Richard B. Berry et al., "The AASM Manual for the Scoring of Sleep and Associated Events: Rules, Terminology and Technical Specifications," Scoring Manual Version 2.2, 2015 American Academy of Sleep Medicine (AASM), 7 pages.

Jacob Cohen, "Weighted Kappa: Nominal Scale Agreement with Provision for Scaled Disagreement or Partial Credit," Psychological Bulletin, vol. 70, No. 4, Oct. 1968, 8 pages.

* cited by examiner

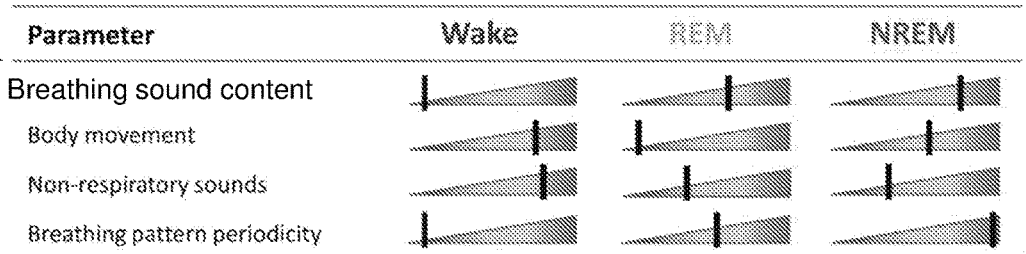
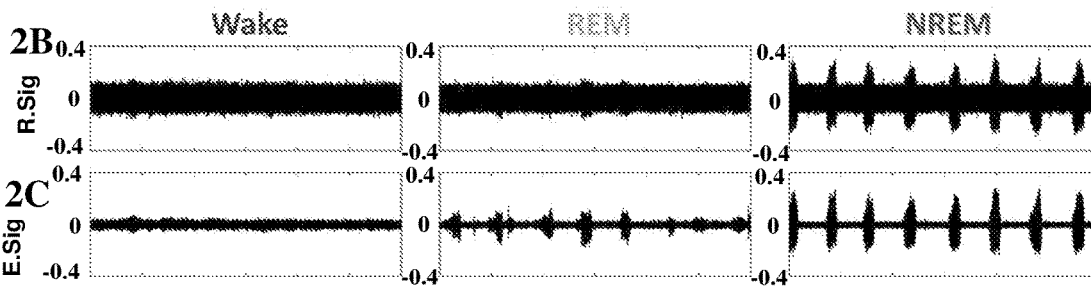
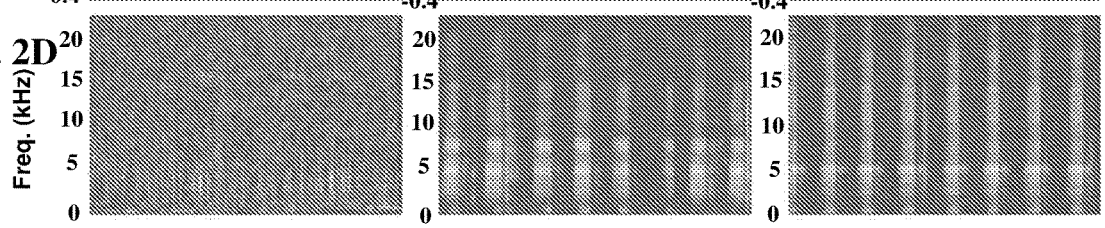
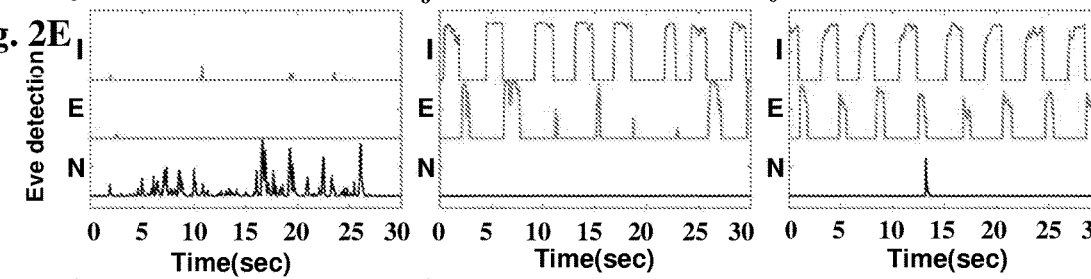
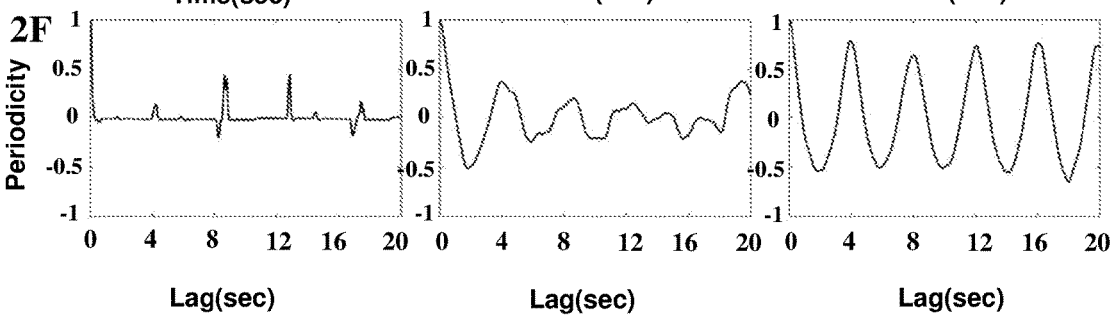

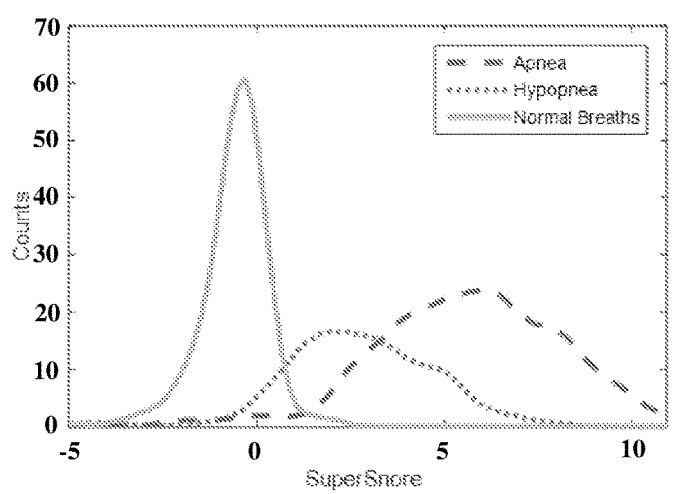
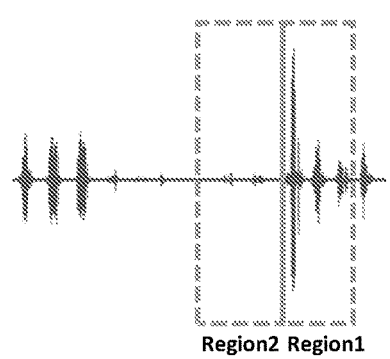
Fig. 8

ESTIMATION OF SLEEP QUALITY PARAMETERS FROM WHOLE NIGHT AUDIO ANALYSIS

This application is the U.S. national phase of International Application No. PCT/IL2017/050786 filed 11 Jul. 2017, which designated the U.S. and claims the benefit of U.S. Application No. 62/360,487 filed 11 Jul. 2016, and U.S. Application No. 62/361,013 filed 12 Jul. 2016, the entire contents of each of which are hereby incorporated by reference.

FIELD OF THE INVENTION

The present invention relates to the field of signal processing. More particularly, the present invention relates to a system and method for analyzing audio signals to detect sleep conditions.

BACKGROUND OF THE INVENTION

During routine sleep diagnostic procedure, sleep is broadly divided into three states: rapid eye movement (REM), non-REM (NREM) states, and wake, frequently named macro-sleep stages (MSS). In order to treat people with sleep disorders, it is important to gather information regarding their MSS during the duration of their sleep.

The gold standard for sleep evaluation is Polysomnography (PSG) that requires a full night stay in a sleep laboratory, while being monitored by a large number of contact-based electrodes and sensors. Sleep is scored by a certified technologist who examines dozens of full-night physiological signals. This procedure is time-consuming and costly. It has long waiting lists and may not be suitable for mass population. It may involve recording the following: electroencephalogram (EEG), electrooculogram (EOG), electromyogram (EMG), electrocardiogram (ECG), air flow, thoracic and abdominal movement, oximetry, body position. Aside from the special and expensive equipment, the trained technician is required to attach the sensors correctly and an expert analyzes the recorded signals for an accurate assessment. The waiting lists for sleep diagnosis are up to several months, due to lack of beds in the sleep centers. The patients are forced to spend a whole night in an unfamiliar environment, attached to various movement-limiting sensors, with an inevitable effect on the sleep quality of the patient. Due to these disadvantages, new methods for sleep estimation are needed that will be more comfortable, non-invasive and have a lower cost.

Non-contact methods for sleep estimation, some audio-based, were developed in order to enable patients to undergo the diagnostic procedure at home.

WO 2013/179254 relates to a method of distinguishing sleep period states that a person experiences during a sleep period. The method comprises: using a non-contact microphone to acquire a sleep sound signal representing sounds made by a person during sleep; segmenting the sleep sound signals into epochs; generating a sleep sound feature vector for each epoch; providing a first model that gives a probability that a given sleep period state experienced by the person in a given epoch exhibits a given sleep sound feature vector; providing a second model that gives a probability that a first sleep period state associated with a first epoch transitions to a second sleep period state associated with a subsequent second epoch; and processing the feature vectors using the first and second models to determine a sleep period state of the person from a plurality of possible sleep period states for each of the epochs.

WO 2012/025892 relates to an apparatus and method for diagnosing obstructive sleep apnea comprising: acquiring a sleep sound signal comprising sounds made by a person during sleep; detecting a plurality of snore sounds in the sleep sound signal; determining a set of mel-frequency cepstral coefficients for each of the snore sounds; determining a characterizing feature for the sleep sound signal responsive to a sum of the variances of the cepstral coefficients; and using the characterizing feature to diagnose obstructive sleep apnea in the person.

WO 2014/115115 relates to determining apnea-hypopnia index (AHI) from speech. The method relates to determining a value for an apnea-hypopnea index (AHI) for a person, comprising: recording a voice track of a person; extracting features from the voice track that characterize the voice track; and processing the features to determine an AHI.

In recent years, efforts have been devoted to seeking alternatives for PSG evaluation. These technologies typically rely on the assumption that movement is associated with wakefulness phase and vice versa. Some approaches evaluate sleep using heart rate variability and even using peripheral arterial tone signals. The most popular method for at home sleep evaluation is wristwatch actigraphy. However, this method estimates a binary decision about sleep and wake patterns and cannot monitor REM. In a previous study [E. Dafna, A. Tarasiuk, and Y. Zigel, "Sleep-Wake Evaluation from Whole-Night Non-Contact Audio Recordings of Breathing Sounds," PloS one, vol. 10, p. e0117382, 2015] it was showed that binary decision of sleep and wake phases can be reliably determined using only breathing sound analysis, showing matched and even superior performances compared to actigraphy-based technologies.

However, there is still a need to provide an efficient, cost effective, comfortable, audio based method and means for determination of sleep parameters (e.g. sleep stages). It is therefore an object of the present invention to provide a method and means for analyzing audio-based features to determinate sleep parameters.

It is a further object of the present invention to provide a method and means using signal-processing to determinate sleep stages.

It is a further object of the present invention to provide a method and means using signal-processing to determinate between apnea hypopnea and normal breathing.

Other objects and advantages of the present invention will become apparent as the description proceeds.

SUMMARY OF THE INVENTION

The present invention relates to estimating sleep quality parameters according to an audio signal of a subject during a sleep duration. The audio signal is processed to obtain the sleep quality parameters. The audio signal is preferably pre-processed to filter out noises. Preferably, a breathing detection may be applied to the signal. The signal is segmented into segments (epochs). Several types of feature parameters may be extracted from each segment by being derived from the segment signal. Several calculations of various signal characteristics may be made to extract the feature parameters.

The feature parameters extracted are inputted into a computing system (e.g. machine learning) which applies a preformed model/function on them to obtain scores (estimated sleep quality parameter) or probability scores of the estimated sleep quality parameters.

According to one embodiment, a whole sleep duration pattern estimation model is applied to the probabilities obtained providing a better "real" result. Then the final sleep quality parameters are extracted for each segment. The whole sleep duration pattern estimation model and the computing system preformed model/function may be generated by training them with a plurality of measurements along with corresponding true result PSG scores.

The present invention relates to a method for determining sleep quality parameters according to audio analyses, comprising:
  obtaining an audio recorded signal comprising sleep sounds of a subject;
  segmenting the signal into epochs;
  generating a feature vector for each epoch, wherein each of said feature vectors comprises one or more feature parameters that are associated with a particular characteristic of the signal and that are calculated according to the epoch signal or according to a signal generated from the epoch signal;
  inputting the generated feature vectors into a machine learning classifier and applying a preformed classifying model on the feature vectors that outputs a probabilities vector for each epoch, wherein each of the probabilities vectors comprises the probabilities of the epoch being each of the sleep quality parameters;
  inputting the probabilities vectors for each epoch into a machine learning time series model and applying a preformed sleep quality time series pattern function on said probabilities vectors that outputs an enhanced probabilities vector for each epoch;
  determining a final sleep quality parameter for each epoch by calculating the most probable sleep quality parameters sequence.

Preferably, the method further comprises carrying out a pre-processing stage comprising noise reduction of the signal.

Preferably, the method further comprises carrying out a breathing detection stage comprising categorizing portions of the signal as breathing and other portions of the signal as non-breathing.

Preferably, the one or more feature parameters are associated with a characteristic selected from the group consisting of breathing sound content, body movements, non-respiratory sounds and breathing pattern periodicity.

Preferably, the one or more feature parameters comprise at least two feature parameters associated with at least two of the characteristics or comprise at least three feature parameters associated with at least three of the characteristics or comprise at least four feature parameters associated with at least four of the characteristics.

Preferably, the one or more feature parameters are all associated with one of the characteristics.

Preferably, the one characteristic is breathing sound content.

Preferably, the one characteristic is body movements.

Preferably, the one characteristic is non-respiratory sounds.

Preferably, the one characteristic is breathing pattern periodicity.

Preferably, the method comprises wherein the feature parameters associated with the breathing sound content characteristic are selected from the group consisting of Respiratory mean SNR feature, Respiratory Frequency centroid, ADmean25, SuperSnore, and XcorrPeak;
  or wherein the feature parameters associated with the body movements characteristic are selected from the group consisting of Body movement percentage feature and Body movement likelihood feature;
  or wherein the feature parameters associated with the non-respiratory sounds characteristic are selected from the group consisting of Non-breathing percentage feature, Non-breathing 90% SNR feature and Non-breathing frequency centroid feature;
  or wherein the feature parameters associated with the breathing pattern periodicity characteristic are selected from the group consisting of Respiratory cycle duty feature, respiratory cycle period feature, respiratory cycle intensity feature and respiratory cycle consistency feature.

Preferably, the one or more feature parameters are each selected from the group consisting of respiratory cycle duty feature, respiratory cycle period feature, respiratory cycle intensity feature, respiratory cycle consistency feature, non-breathing percentage feature, respiratory mean SNR feature, respiratory frequency centroid feature, non-breathing 90% SNR feature, non-breathing frequency centroid feature, ADmean25, SuperSnore and XcorrPeak.

Preferably, the method further comprises an initial stage of generating the preformed classifying model comprising:
  obtaining audio recorded signals comprising sleep sounds of a plurality of subjects;
  segmenting the signals into corresponding epochs;
  generating a feature vector for each epoch, wherein each of said feature vectors comprises one or more feature parameters that are associated with a particular characteristic of the signal and that are calculated according to the epoch signal or according to a signal generated from the epoch signal;
  inputting the generated feature vectors of each subject into a machine learning classifier along with corresponding true result annotated sleeping scores;
  generating the preformed classifying model according to machine learning.

Preferably, the preformed sleep quality time series pattern function is generated according to the following steps:
  inputting into a machine learning model a plurality of true result hypnograms divided into epochs, wherein each hypnogram comprises a sleep quality parameters result for each of its epochs;
  applying machine learning on said plurality of true result hypnograms taking into account the epoch time sequences, and the sleep quality parameters at each epoch time sequence.

Preferably, the sleep quality parameters are macro sleep stages selected from the group consisting of WAKE, REM and NREM.

Preferably, calculating the most probable sleep quality parameters sequence is carried out by using the Viterbi algorithm.

Preferably, the method further comprises an initial step of recording the audio signal.

Preferably, the sleep quality parameters are sleep-disordered breathing parameters selected from the group consisting of apnea, hypopnea and normal breathing.

The present invention relates to a system for determining sleep quality parameters according to audio analyses, comprising:
  a processor;
  a memory coupled to the processor and configured to store program instructions executable by the processor to implement the method for determining sleep quality parameters according to audio analyses, comprising:

obtaining an audio recorded signal comprising sleep sounds of a subject;

segmenting the signal into epochs;

generating a feature vector for each epoch, wherein each of said feature vectors comprises one or more feature parameters that are associated with a particular characteristic of the signal and that are calculated according to the epoch signal or according to a signal generated from the epoch signal;

inputting the generated feature vectors into a machine learning classifier and applying a preformed classifying model on the feature vectors that outputs a probabilities vector for each epoch, wherein each of the probabilities vectors comprises the probabilities of the epoch being each of the sleep quality parameters;

inputting the probabilities vectors for each epoch into a machine learning time series model and applying a preformed sleep quality time series pattern function on said probabilities vectors that outputs an enhanced probabilities vector for each epoch;

determining a final sleep quality parameter for each epoch by calculating the most probable sleep quality parameters sequence.

The present invention relates to a method for determining sleep quality parameters according to audio analyses, comprising:

obtaining an audio recorded signal comprising sleep sounds of a subject;

segmenting the signal into epochs;

generating a feature vector for each epoch, wherein each of said feature vectors comprises one or more feature parameters that are associated with a particular characteristic of the signal and that are calculated according to the epoch signal or according to a signal generated from the epoch signal;

inputting the generated feature vectors into a machine learning classifier and applying a preformed classifying model on the feature vectors that outputs a probabilities vector for each epoch, wherein each of the probabilities vectors comprises the probabilities of the epoch being each of the sleep quality parameters;

determining a final sleep quality parameter for each epoch;

wherein the one or more feature parameters are associated with a characteristic selected from the group consisting of body movements and non-respiratory sounds.

In another embodiment—all the feature parameters are associated with body movements. In another embodiment—all the feature parameters are associated with non-respiratory sounds.

Preferably, the method further comprises:

inputting the probabilities vectors for each epoch into a machine learning time series model and applying a preformed sleep quality time series pattern function on said probabilities vectors that outputs an enhanced probabilities vector for each epoch;

wherein determining the final sleep quality parameter for each epoch by calculating the most probable sleep quality parameters sequence.

The present invention relates to a system for determining sleep quality parameters according to audio analyses, comprising:

a processor;

a memory coupled to the processor and configured to store program instructions executable by the processor to implement the method for determining sleep quality parameters according to audio analyses, comprising:

obtaining an audio recorded signal comprising sleep sounds of a subject;

segmenting the signal into epochs;

generating a feature vector for each epoch, wherein each of said feature vectors comprises one or more feature parameters that are associated with a particular characteristic of the signal and that are calculated according to the epoch signal or according to a signal generated from the epoch signal;

inputting the generated feature vectors into a machine learning classifier and applying a preformed classifying model on the feature vectors that outputs a probabilities vector for each epoch, wherein each of the probabilities vectors comprises the probabilities of the epoch being each of the sleep quality parameters;

determining a final sleep quality parameter for each epoch;

wherein the one or more feature parameters are associated with a characteristic selected from the group consisting of body movements and non-respiratory sounds.

Optionally, the breathing detection comprises identifying inhale and exhale episodes and their respective sound properties.

BRIEF DESCRIPTION OF THE DRAWINGS:

The present invention is illustrated by way of example in the accompanying drawings, in which similar references consistently indicate similar elements and in which:

FIG. 2A illustrates the relative effect of each parameter on a sleep stage according to an embodiment of the present invention.

FIG. 2B shows 30 sec of Raw audio signal amplitude according to an embodiment of the present invention.

FIG. 2C shows the enhanced audio signal following noise suppression according to an embodiment of the present invention.

FIG. 2D shows a spectrogram of the signal in FIG. 2C.

FIG. 2E shows the detection of inhale, exhale and non-respiratory sound expressed as a likelihood score according to an embodiment of the present invention.

FIG. 2F shows a periodicity measurement calculated as autocorrelation function of the detected breathing curves in FIG. 2E.

FIG. 8 shows an example of the Supersnor distribution.

Figure 1:
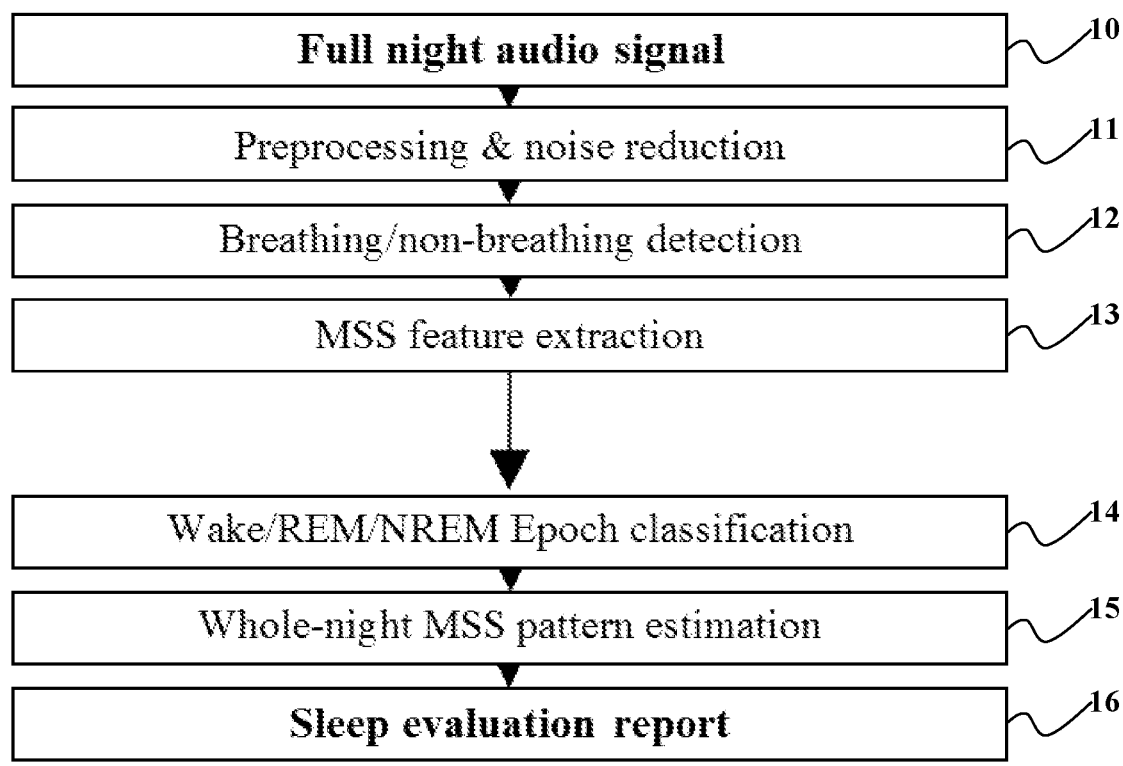
FIG. 1 illustrates an embodiment of the method stages of the present invention.

DETAILED DESCRIPTION OF THE INVENTION:

The present invention relates to evaluating sleep stages according to audio analyses due to the differences in sound properties within each MSS enabling separation between them. Some properties differences are respiratory-related sounds due to alternation of upper airways patency during each MSS, and some involve sounds of body movements in bed.

The present invention is based on recording sound of a user patient in a non-contact manner and based on analysis of acoustic features extracted from the audio signals recorded.

The present invention comprises a technology of whole night audio recordings. The present invention system comprises a recorder device preferably with a microphone wherein the microphone is typically placed in proximity to a sleeping person (optionally, in a bedroom of his own house) for a full sleep sound recording. The microphone is configured to register sounds made by the person during sleep and sounds that are not made by the person that reache the microphone. Sounds that are made by the person comprise for example, snoring sounds, breathing, coughing and voice sounds, and sounds that are produced by motion of the person, such as bed creaking and blanket rustling sounds. Sounds that are not made by the person may comprise street sounds and sounds originating in other rooms of the person's house that reach the bedroom and sounds made by appliances, such as a whirring sound made by an overhead fan in the bedroom. Sounds that are registered by the microphone that are not respiratory sounds (that are not snoring and breathing sounds) are referred to as background sounds. Various recorders may be used. An example of a digital audio recorder device is model EDIROL R-4 (Roland, 2-7 Kandasuda-cho, Chiyoda-ku, Tokyo 101-0041, Japan). An example of a microphone is ambient microphone RØDE NTG-1 (107 Carnarvon St, Silverwater, NSW, 2128 Australia).

The microphone (and recorder) transmits the sounds that it registers to a computer system. The computer system comprises a processor configured to processes the sleep sound signals to identify breathing sound durations therein and classify the sounds (e.g. breathing sound durations) as REM, NREM and WAKE periods. The computer system comprises a memory in which it stores the sleep sound signals that the computer system receives from the microphone. The computer system (e.g. by use of the processor) is configured to carry out computer executable instruction sets relating to at least one operation selected from pre-processing, noise reduction, breathing/ non-breathing detection, segmentation, feature extraction, model estimation, data comparison to a preformed model, carrying out machine learning tasks (e.g. classification), as all will be explained in detail herein.

The computer system may comprise a PC, a smart phone, a laptop, and/or a work book that stores and executes the instruction sets defined herein. However, the computer system is not limited to being housed in a single computer, or a computer located in a same room with the sleeping person. Computer system may be a distributed system having components and executable instruction sets located in different servers, and may be partially or completely based on access to servers via the internet, that is partially or completely "cloud based".

An audio signal is a representation of sound, typically as an electrical voltage. Audio signals may be characterized by parameters such as their bandwidth, power level in decibels (dB) and voltage level. A preferred audio signal suitable for breathing analysis is a signal powerful enough so that most of the breathing sound-events characteristics are included and preserved.

Since the acquisition of the audio signal through a microphone (and recorder) is analogue, its digitization is necessary to perform computational processing. The present invention method may comprise recording an individual user during a sleep time (typically a nocturnal sleep time) to obtain sleep sound signals.

The present invention method comprises obtaining a recorded audio signal 10 of a subject during his time of sleep (as can be shown in FIG. 1). The method comprises a pre-processing stage 11 (of the audio signal) comprising a signal digitization. The audio signals are recorded at a sampling frequency preferably of 16-96 kHz, at preferably 8-32 bits per sample, PCM and stored in the computer.

Typical recordings of the present invention are of long audio signals (e.g. 7-9 hours) aimed to acquire full night sleep recordings. The audio files generated may be large files. Processing and analyzing such large files would require very high computational power and may result in very long computation time. Hence, optionally, as a pre-processing act, the signals may be down sampled, creating more convenient and manageable files at the cost of the loss of information in the high frequencies (e.g. >8kHz).

The pre-processing stage may further comprise a signal enhancement (noise reduction). This may comprise removing background sounds from a received audio signal, e.g. removing noises that are not respiratory sounds (snoring and breathing sounds) or body movements.

The noise reduction may be performed by a variety of methods. According to a preferred embodiment the raw whole-night audio signal is enhanced (signal-to-noise manner) by an adaptive noise reduction algorithm based on a spectral subtraction approach (e.g. E. Dafna, A. Tarasiuk, and Y. Zigel, "*Automatic Detection of Whole Night Snoring Events Using Non-Contact Microphone*," PLoS One, vol. 8, p. e84139, 2013). This step is important since it reduces the background noise, which is subject-independent, and emphasizes the transient events that were recorded during sleep such as quiet breaths and body movements.

The present invention method may further comprise a breathing/non-breathing detection stage 12 categorizing portions of the signal as breathing and other portions of the signal as non-breathing. A breathing detection system (that may be used with the present invention) was developed that is capable of detecting very low energy audio events and distinguishing between breathing and non-breathing episodes [E. Dafna, A. Tarasiuk, and Y. Zigel, "*Automatic Detection of Whole Night Snoring Events Using Non-Contact Microphone*," PLoS One, vol. 8, p. e84139, 2013, and T. Rosenwein, E. Dafna, A. Tarasiuk, and Y. Zigel, "*Detection of breathing sounds during sleep using non-contact audio recordings*," Conf Proc IEEE Eng Med Biol Soc., 2014]. Non-breathing events may be categorized into three categories: 1) vocally self-generated sounds such as talking, coughing, moaning, and mumbling; 2) body movement sounds such as linen, pillow, and clothes rubbing and twitching; and 3) third party sounds such as door slams, cars, dogs, TV, etc. The output of the detector is the exact time location of each audio event captured. As an example, if there is a movement noise (above a certain threshold) the probability of determination of a breathing noise decreases. The sensitivity of capturing quiet audio events may be as low as 20 dB. The preferable sensitivity is above 20 dB (sound pressure level-SPL), meaning higher than ¹/₁₀ of the background noise level in a standard bedroom.

The present invention further comprises a segmentation stage (typically carried out once the whole night audio signal is enhanced). The signal is divided into intervals (epochs) across the night. Most preferably the epochs are of 30 seconds, yet any interval of capturing several breathing cycles is suitable, e.g. 8 sec to 1 min.

The present invention method further comprises a feature extraction stage 13. From each epoch, several features may be extracted designed to discriminate between the three classes of MSS: Wake, REM, and NREM. Each of the features extracted are calculated from the epoch signal (or a signal generated from the epoch signal such as a breathing pattern signal generated by a breathing detector). Several features may be extracted. The features may be categorized into groups, wherein each group is associated with a particular characteristic of the signal.

Alterations in MSS are associated with changes of physiological parameters relating to characteristics such as:
  breathing sound content (typically affected by the upper airway resistance during sleep causing higher respiratory sounds);
  body movements;
  non-respiratory sounds such as coughing, itching, murmurs etc.;
  breathing pattern periodicity.

All these characteristics are associated with recognizable sounds that could be detected and analyzed. FIGS. 2A-2E show examples of the effect of these characteristics on the probability of being in a WAKE, REM or NREM stage. FIG. 2A shows the relative effect of each parameter on a sleep stage (black rectangle on the location of the triangle height increasing from left to right, marking the relative effect). For a weak effect the black rectangle would be on the left (low) side of the triangle; for a strong effect the black rectangle would be on the right (high) side of the triangle. For example, body movement is absent in REM, high during wake and lower during NREM.

FIG. 2B shows 30 sec (x axis) of Raw audio signal amplitude (y axis) (R. sig in the figure being raw audio signal).

FIG. 2C shows the enhanced audio signal (corresponding to the signal in FIG. 2B) following noise suppression (E. sig in the figure being enhanced audio signal).

FIG. 2D shows a spectrogram of the signal in FIG. 2C. Brighter colors represent higher sound intensity. The X axis is time in seconds and the Y axis is frequencies (in KHz).

FIG. 2E shows the detection of inhale (upper graph of the three), exhale (middle graph) and non-respiratory sound (bottom graph) expressed as a likelihood score. Higher values (upright) indicate higher likelihood score ("Eve. Detection" in the figure being event detection).

FIG. 2F shows a periodicity measurement calculated as autocorrelation function of the detected breathing curves in FIG. 2E. The periodic pattern is noticeable in NREM, decreased in REM and almost absent in WAKE.

FIGS. 2B-2F show a single representative epoch (30 sec) during wake, REM and NREM, from a 53 year old male, having a BMI of 27 and an AHI of 16.

The breathing characteristics features (e.g. the features associated with the breathing sound content characteristic and the features associated with the breathing pattern periodicity characteristic) are obtained via an analysis of the breathing pattern of a subject. The breathing pattern of a subject can be obtained e.g. by a breathing detector (breathing detection system) as described hereinabove to effectively detect the events of interests. For this, the epoch signals that are used for calculations are the "breathing event" detected signals. The breathing-related features may be extracted from the breathing pattern signal (generated from the breathing detector) of each epoch.

Breathing Pattern Periodicity Features:

The following features are examples of features associated with the breathing cycle (and are extracted by using the breathing detector). A breathing likelihood function (B[n]) for each epoch, is described herein in relation to the following functions to better understand the present invention. This breathing likelihood function ranges from 0 to 1 (low to high likelihood), presenting the likelihood of a breathing event to occur in a given time index (n) within the epoch (a total of N time indexes in the epoch).

1) Respiratory cycle duty feature—this feature measures the time proportion of breathing effort in an epoch relative to the respiratory cycle duration of the epoch. An example of its calculation is:

$$\text{duty\_cycle} = \frac{1}{N} Bool(B[n] > 0.5),$$

where, $Bool$ is the boolean operator of true = 1, and false = 0.

2) Respiratory cycle period feature—this feature measures the average respiratory cycle duration based on autocorrelation approach. An example of its calculation "Period" is:

$$\text{Period} = \arg\max_k (R[k]) \Big|_{k \in [2,6]sec}$$

$$R[k] = \frac{1}{N-k} \sum_{n=1}^{N-k} (B[n] - \overline{B}) \times (B[n+k] - \overline{B})$$

$$\overline{B} = \frac{1}{N} \sum_{n=1}^{N} B[n]$$

k is the "lag" interval in sec (sample). The duration between 2 and 6 seconds is within a reasonable range for the breathing of a subject.

3) Respiratory cycle intensity feature—this feature is determined by the value of the autocorrelation first peak. An example of its calculation is:

Intensity=max $([k])|_{k \in [2,6]sec}$

4) Respiratory cycle consistency feature—measures the homogeneity of the respiratory cycles. This relates to how much the cycle applies to each breath, and not only an average of the whole epoch. An example of its calculation is:

Consistency=std (peaks(R))

Breathing Sound Content Features:

The following features are examples of features associated with the breathing sound content (typically affected by the upper airway resistance during sleep causing higher respiratory sounds). Items B[n], N and n are as described hereinabove. These breathing sound content features are extracted by using the breathing detector.

1) Respiratory mean SNR feature—measures the average signal-to-noise ratio (dB scale) of all respiratory events detection. An example of its calculation is:

$$\text{Mean\_SNR} = \frac{1}{N} \sum_{n=1}^{N} SNR(B[n] > 0.5),$$

where, $SNR$ is the temporal ratio between breathing and background noise signal 2) Respiratory Frequency centroid—is the average frequency centroid of all breathing detected (similar to center of mass function). An example of its calculation is:

$$\text{Centroid} = \frac{1}{N} \sum_{n=1}^{N} \left[ \int_{f=0}^{\frac{Sampeling\ rate}{2}} f \times X(f, B[n] > 0.5) \right],$$

where, $X(f, n)$ is the temporal ($n$) discrete Fourier transform ($DFT$), $f$ is frequency in kHz 3) ADmean25

During normal breathing segments, time signal amplitude varies significantly, in comparison to hypopnea events and apnea events, and its differentiation provides high values.

$$SortBreathSNR = sort(SNR(B[n] > 0.5))$$

$$Len = \sum_{i=0}^{N} Bool(B[n] > 0.5)$$

$$ADmean_{25} = \frac{1}{\lfloor N \times 0.75 \rfloor} \sum_{i=\lfloor N \times 0.75 \rfloor}^{Len} SortBreathSNR(n) - \frac{1}{\lceil N \times 0.25 \rceil} \sum_{i=1}^{\lceil N \times 0.25 \rceil} SortBreathSNR(n)$$

4) SuperSnore

At the end of an apnea or a hypopnea event there might be a loud breath or snore that is supposed to compensate for the lack of oxygen caused by the cessation of breathing. This feature compares the maximal short-term energy in the 5-second window after the event terminates, with the maximal short-term energy during the event itself. FIG. 8 shows an example of the Supersnore distribution.

$$SuperSnore = \frac{\max(SNR(B[n] > 0.5)|_{n \in Region1})}{\max(SNR(B[n] > 0.5)|_{n \in Region2})},$$

Region1, is the suspected 5 seconds containing breathing events

Region2, is the suspected 5 seconds before resuming breathing,

Higher values will indicate a ceassesions of breathing presumably by apnea.

5) XcorrPeak

The autocorrelation function of the short-term energy sequence among hypopnea and normal breath events tends to resemble a sine wave. Utilizing this tendency, XcorrPeaks is computed using the correlation coefficient achieved from applying a 0.3 hertz sine wave curve fitting to the mentioned autocorrelation function.

$$R[k] = \frac{1}{N-k} \sum_{n=1}^{N-k} (B[n] - \overline{B}) \times (B[n+k] - \overline{B}),$$

$$SyntBreath[k] = \cos[2\pi \times 0.3 \times k \times 0.05]$$

$$XcorrPeaks = \frac{\left( \sum_{k=1}^{N} (R[k] - \overline{R})(SyntBreath[k] - \overline{SyntBreath}) \right)^2}{\sum_{k=1}^{N} (R[k] - \overline{R})^2 \times \sum_{k=1}^{N} (SyntBreath[k] - \overline{SyntBreath})^2}$$

Body Movement Features:

The following features are examples of features associated with the subject's body movement. These features are extracted from the epoch signal without the breathing detection stage. Body movement is usually associated with wakefulness, i.e., the same assumption used in actigraphy devices. Moreover, REM is characterized by a paralyzed-limbs phenomenon, which prevents the patient from harming himself during dreaming; therefore, REM epochs will usually contain fewer body movements.

1) Body Movement Percentage Feature

This feature is calculated as the ratio between all body movement detected durations combined relative to the epoch duration (e.g. 30 sec epoch duration). An example of its calculation is:

$$\text{percentage} = \frac{1}{N} \sum_{n=1}^{N} Bool(BodyMove[n] > 0.5),$$

where, $Bool$ is the boolean operator of true = 1, and false = 0.

2) Body Movement Likelihood Feature

This feature is calculated as the average of all detected body movement likelihood score. An example of its calculation is:

$$BM\_likelihood = \frac{\sum_{n=1}^{N} BodyMove[n] \times Bool(BodyMove[n] > 0.5)}{\sum_{n=1}^{N} Bool(BodyMove[n] > 0.5)},$$

where, $Bool$ is the boolean operator of true = 1, and false = 0.

Non-Respiratory Sounds Features:

The following features are examples of features associated with the epoch portions where non-breathing is detected. These features may be extracted from the epoch signal by using the breathing detector (which can also function as a "non-breathing detector").

1) Non-Breathing Percentage Feature

This feature is calculated as the ratio between all non-breathing detected durations combined relative to the epoch duration (e.g. 30 sec epoch duration). An example of its calculation is:

$$\text{percentage} = \frac{1}{N}\sum_{n=1}^{N} Bool(\text{Noise}[n] > 0.5),$$

where, *Bool* is the boolean operator of true = 1, and false = 0. "Noise[n]" being likelihood function of non-breathing.

2) Non-Breathing 90% SNR Feature

This feature represents the SNR value of the 10% upper percentile of all non-breathing detected. The noise events (not background noises) are detected using the breathing detector mentioned above, as the non-breathing classification.

3) Non-Breathing Frequency Centroid Feature

This feature is calculated in a similar manner as for the breathing frequency centroid (mutatis mutandis). An example of its calculation is:

$$\text{Centroid} = \frac{1}{N}\sum_{n=1}^{N}\left[\int_{f=0}^{\frac{\text{Sampeling rate}}{2}} f \times X(f, B[n] > 0.5)\right],$$

where, $X(f, n)$ is the temporal ($n$) discrete Fourier transform (*DFT*), $f$ is frequency in kHz.

For each of the epochs a specific feature vector having a number of dimensions as the number of extracted features (each feature representing one of the dimensions) is generated. Each feature vector comprises all of the extracted features (e.g. calculated from the epoch signal) of its particular epoch. These features assist to distinguish Wake, REM and NREM, as will be explained herein.

The present invention method comprises a classification step 14. The feature vector (of each epoch) is inputted into a machine learning classifier. The machine learning classifier applies functions on the inputs according to a preformed model (that was previously generated, as will be explained hereinafter), and then outputs a decision determination for each epoch—Wake, REM or NREM.

According to an embodiment of the present invention the classifier calculates and outputs (according to the preformed model) a 3×1 state probabilities vector providing the probability of each epoch being WAKE, being REM and being NREM (and not only concluding the final determined MSS which is the one with the highest probability).

The preformed model is created by using a plurality of subjects that over go an all-night testing where different measurements are applied on them. First, a training phase is commenced using a supervised learning approach, by training the classifiers using PSG (typically manually) annotated sleeping scores. The measurements and calculation steps may comprise:

1) Carrying out a microphone recording, pre-processing/noise reduction, breathing/non-breathing detection and feature extraction as explained herein. The features for each epoch are inputted into the classifier.

2) Applying PSG measurements and dividing the measurements into epochs corresponding to the recording epochs (i.e. each epoch duration on the recording timeline is equal to its corresponding PSG epoch, both on the same timeline), wherein for each epoch a determination is made based on the PSG measurements that the epoch represents Wake, REM or NREM. Typically, the determination of each PSG epoch is carried out by a certified technician following standard scoring rules (e.g. C. Iber, S. Ancoli-Israel, C. A. L., and S. Quan, *The AASM Manual for the Scoring of Sleep and Associated Events: Rules, Terminology, and Technical Specifications*, 1ed. Westchester, Ill.: *The American Academy of Sleep Medicine*, 2007.).

Then, the feature vector for each recording signal epoch is inputted into the classifier along with the corresponding "true results" determination, i.e. the corresponding PSG epoch determination. This is carried out for all of the vectors and corresponding PSG epoch determinations of all of the plurality of subjects. The machine learning classifier thus creates a model that can classify a similar vector with the same number of dimensions (representing a single epoch) inputted thereto—classifying the vector as Wake, REM or NREM.

Then, a validation phase is applied with a plurality of subjects having recording signals and corresponding PSG determination results. The feature extractions of the recording signal epochs (after pre-processing/noise reduction, breathing/non-breathing detection, etc., as explained herein) are inputted into the classifier and the output thereafter to the "true result enhancing feature"—the time series function model (as will be explained hereinafter) to produce the final output determinations. These output determinations are compared with the corresponding PSG determination results and thus a success percentage is extracted.

More specifically, for each subject from the validation dataset a comparison is carried out epoch-by-epoch between the manually annotated PSG sleep scoring against the automated audio-based analysis (ABA) sleep scoring (the final output of the second machine learning model). Two agreement measurements were calculated, 1) simple accuracy, i.e, the number of agreed (match) epochs divided by the overall epochs, e.g. according to Cohen's kappa (J. Cohen, "Weighted kappa: Nominal scale agreement provision for scaled disagreement or partial credit," Psychological bulletin, vol. 70, p. 213, 1968). In addition, we compared the sleep quality parameters calculated from PSG and from the audio-based-analysis (ABA) approach using mean difference (subtraction), mean error (absolute difference), and two-tail paired t-test, in order to examine the validity of the ABA on clinical decisions.

In order to train the model, for each epoch the PSG annotation (given by the technologist) was matched with the determined corresponding acoustic features. Then, based on the statistical information (presented in the features) associated within each stage, the model converges into optimized state which discriminate between the stages. Once the model was trained (model parameters/coefficients), a new epoch is processed to calculate the inputted features. These inputted features (e.g. being numbers) are fed into the classifier and a 3D score is calculated.

Figure 3A:
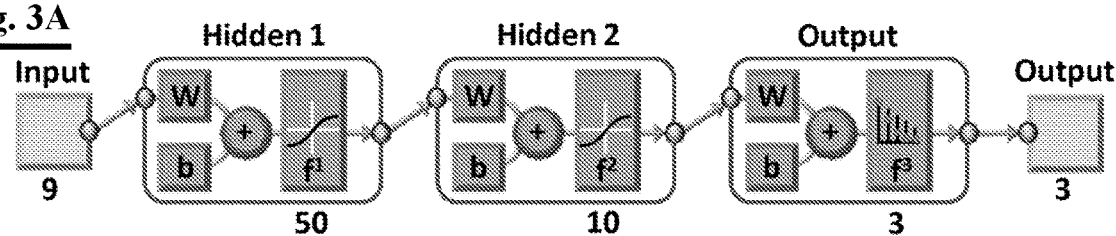
FIG. 3A shows a feed-forward neural network configuration according to an embodiment of the present invention.

According to a preferred embodiment the classifier is an artificial neural network (ANN) classifier with inputs (the extracted features) that projects the decision into a 3D score (3 states). Each dimension in the output represents a likelihood score for a specific class (Wake/REM/NREM). A preferred example includes a 'feed-forward' neural network architecture with two hidden layers composed of 50 and 10 hyperbolic tangent sigmoid neurons, respectively, followed by a 'softmax' transfer function for the output layer. FIG. 3A shows the feed-forward neural network configuration. The output of the ANN classifier, p(x), can be written as:

$$p(x)=f_3(W_3f_2(W_2f_1(W_1x+b_1)+b_2)+b_3)$$

where p is a 3-class score; x is the input vector, i.e., feature set; $f_i$ is the $i^{th}$ transfer function, with its corresponding weights $W_i$; and bias values $b_i$. An example of an ANN setup can be found in Y. Anzai, *Pattern Recognition & Machine Learning:* Elsevier, 2012.

Figure 3B:
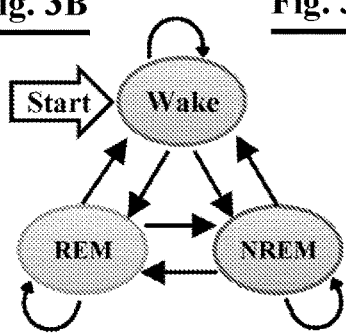
FIG. 3B shows a diagram according to an embodiment of the present invention.

Once each epoch classification is determined (represented by either one of three scores—wake, REM, and NREM), a preformed time series (function) model is applied 15 to each of the determined results (the MSS probabilities vector for each epoch) that enhances the correctness of the determined MSS or changes the determined MSS. This time series function model takes into account a whole-night MSS pattern estimation and affects the final outcome accordingly. The purpose of this model is to enhance correctness by inserting additional knowledge (in relation to the time series) that estimates a more realistic sleep pattern sequence. The time series function model is preformed (previously generated) by a machine learning model. An example of a machine learning model used that may generate the time series function model is a three-state time-dependent hidden Markov model (HMM) (e.g. as used in Y. Anzai, *Pattern Recognition & Machine Learning:* Elsevier, 2012). FIG. 3B shows a diagram of one state capable of transitioning to either one of the other states or remaining in the same state.

In this configuration, the transition probability between each state varies along time, i.e., across the night. For example, one would expect that at the beginning, transitions will pull toward wakefulness, while in the middle of the night toward REM and NREM. The probability for a given epoch n to be classified into each of the three states can be calculated using the following equation:

$$s_{n+1} = T_n \times p_{n+1},$$

where $s_{n+1}$ is the 3×1 estimated state probabilities vector of a given epoch n+1. $T_n$ is a 3×3 preformed transition matrix at a given epoch n, and $p_{n+1}$ is the 3×1 state probabilities vector of an epoch n+1 estimated by the first classifier (e.g. ANN classifier), i.e., determined by the acoustic features. Thus, each epoch after the calculation has a corresponding estimated state probabilities vector indicating the probability of each one of the 3 MSSs.

Three classes across N epochs yield $3^N$ possible state sequences. Each of the MSS may follow a previous MSS (as shown in FIG. 3B). The most probable state sequence is represented by the maximum probability—Pr score. The present invention method comprises determining the maximum Pr score by calculating the most probable sequence. A Viterbi algorithm (e.g. as explained in Y. Anzai, *Pattern Recognition & Machine Learning:* Elsevier, 2012) may be applied to find the maximum Pr score efficiently, i.e, the most likely sleep pattern sequence.

According to one embodiment, for a given states sequence—$(\sigma_1, \sigma_2, \ldots, \sigma_N) \in \{Wake, REM, NREM\}$, the probability value may be calculated using the following equation:

$$Pr(s_1 = \sigma_1, s_2 = \sigma_2, \ldots, s_N = \sigma_N) = \prod_{n=1}^{N} (s_n = \sigma_n),$$

Figure 3C:
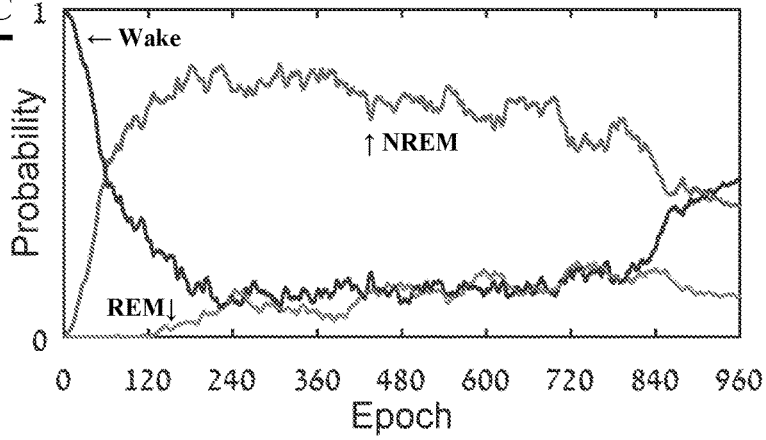
FIG. 3C shows an example of the probability of each MSS during the night according to an embodiment of the present invention.

Thus a final output is generated comprising the final Macro Sleep Stages determined for each epoch. FIG. 3C shows an example of the probability of each MSS during the night. It should be noted that the curves in the figure were generated solely by state transition probabilities and regardless of the epoch's score, hence presenting the global states probability, a most probable sleeping pattern for humans.

The preformed time series model is previously generated by inputting into a machine learning model a plurality of hypnogram results. Each hypnogram comprise an MSS result for each of its epochs (of a whole sleep duration), all which are inputted into the machine learning model. Thus a plurality of MSS results are provided for each sequence epoch of the sleep durations, i.e. the machine learning model receives a plurality of MSS results for a first sleep epoch, then for a second sleep epoch, etc. The machine learning model generates a sleep pattern affecting function (e.g. transition matrix) accordingly taking in to account the sleep pattern. Thus a transition matrix for each epoch may be generated, providing certain affecting weights for each epoch of the epoch sequences.

An example of a machine learning model used is a time-dependent hidden Markov model (HMM).

The output of the epoch final determinations are extracted and generate a whole-night MSS hypnogram. Thus a clinical sleep evaluation report 16 can be generated. According to a specific embodiment of the present invention, seven sleep parameters may be assessed. These sleep parameters are used in a standard polysomnography test [AASM guidelines]. In order to evaluate sleep and its disorders, sleep quality parameters such as the following may be determined (by using the determined hypnogram):

1) total sleep time (TST)—the overall duration of sleep stages, 2) sleep latency (SL)—the time span between lying in bed and the start of sleeping, 3) sleep efficiency (SE)—the ratio between TST and total time in bed, 4) wake-time after sleep onset (WASO)—the summation of all awakening episodes during sleep, 5) awakening index (AwI)—the average number of awakenings per hour of sleep, 6) REM latency (RL)—the time span between sleep onset and the first REM cycle, and 7) REM percentage (RP)—the ratio between REM duration and TST.

EXAMPLE 1

Audio signals of 35 patients referred to a sleep laboratory were recorded and analyzed. An additional 178 subjects were used to train a probabilistic time-series model for MSS staging across the night. The audio-based system was validated on 20 out of the 35 subjects. System accuracy for estimating (detecting) epoch-by-epoch wake/REM/NREM states for a given subject is 74% (69% for wake, 54% for REM, and 79% NREM). Mean error (absolute difference) was 36±34 min for detecting total sleep time, 17±21 min for sleep latency, 5±5% for sleep efficiency, and 7±5% for REM percentage. These encouraging results indicate that audio-based analysis can provide a simple and comfortable alternative method for ambulatory evaluation of sleep and its disorders.

Sleep data, from 213 patients (>18 years) who were scheduled for routine PSG study at the sleep-wake disorder unit at Soroka University Medical Center, was prospectively acquired. Thirty-five of them were simultaneously recorded with a digital audio recorder device (EDIROL R-4) and an ambient microphone (RØDE NTG-1). The microphone was attached to the ceiling and hung about one meter above the subject's head. Subjects' characteristics are summarized in Table 1. Audio signals were recorded at a sampling frequency of 16 kHz, 16 bits per sample, PCM and stored with the PSG sleep manual scoring by a certified technologist. The raw audio signal was then processed off-line using the present invention method, which is shown in FIG. 1.

TABLE 1

Patient Characteristics.

| Parameter | Design (HMM) | Design (ANN) | Validation (ANN + HMM) |
|---|---|---|---|
| # of Patients | 178 | 15 | 20 |
| Male/Female | 108/70 | 10/5 | 13/7 |
| Age | 55 ± 15 | 49 ± 13 | 53 ± 14 |
| (years) | 19-87 | 25-66 | 23-70 |
| BMI | 32 ± 6 | 29 ± 6 | 35 ± 5 |
| (kg/m2) | 20-58 | 23-45 | 25-45 |
| AHI | 21 ± 18 | 17 ± 10 | 20 ± 13 |
| (events/hr) | 0-88 | 2-34 | 5-52 |
| # of Epochs | 866 ± 55 | 920 ± 62 | 870 ± 75 |
| | 560-987 | 782-1007 | 720-1025 |

BMI—Body mass index, AHI—Apnea and hypopnea index. Values are mean ± SD, and range min-max.

An overall accuracy of 95% was reported for breathing detection and 98% for non-breathing detection; sensitivity of capturing quiet audio events as low as 20dB was reported. The signal was divided into 30s intervals (epochs) across the night.

From each epoch, nine features were extracted designed to discriminate between the three classes of MSS: Wake, REM, and NREM. The applied the breathing detector described herein was applied to effectively detect the events of interests.

The extracted features were:
1) Respiratory cycle duty feature;
2) Respiratory cycle period feature;
3) Respiratory cycle intensity feature;
4) Respiratory cycle consistency feature;
5) Non-breathing percentage feature;
6) Respiratory mean SNR feature;
7) Respiratory Frequency centroid feature;
8) Non-breathing 90% SNR feature;
9) Non-breathing frequency centroid feature.

An artificial neural network (ANN) classifier was used for the MSS classification, having 9D inputs that projects the decision into a 3D score (3 states). A 'feed-forward' neural network architecture with two hidden layers composed of 50 and 20 hyperbolic tangent sigmoid neurons, respectively, followed by a 'softmax' transfer function for the output layer, was used.

A three-state time-dependent hidden Markov model (HMM) was used for the whole night pattern machine learning model. A Viterbi algorithm was used to find the maximum Pr score efficiently.

Training phase—The classifiers were trained using manually annotated sleeping scores. The sleeping annotations involve three MSS (Wake, REM, and NREM) across the night determined by a sleep expert following the standard scoring rules. The ANN classifier training process was conducted on the annotated sleep-scoring of 15 subjects as shown Table 1.

For the time-series HMM, an estimation was made for the state transition matrix (probabilities) for the MSS patterns based on the annotated sleep scores of 178 subjects, listed in Table 1. These transitions are time dependent and were estimated for each state and for each time index (epoch) across the night.

Validation phase—For the validation phase, an estimation was made for the MSS patterns of 20 subjects, and respectively compared to the manually annotated MSS (Shown in Table 1). The most probable MSS sequence for a subject was estimated using the Viterbi algorithm.

System Performance Evaluation

For each subject from the validation dataset (Table 1), epoch-by-epoch was compared between the manually annotated PSG sleep scoring against the automated audio-based analysis (ABA) sleep scoring. Two agreement measurements were calculated, simple accuracy and Cohen's kappa. Moreover, these parameters, calculated from PSG and from the audio-based-analysis (ABA) approach, were compared using mean difference (subtraction), mean error (absolute difference), and two-tail paired t-test.

Results

Figure 4:
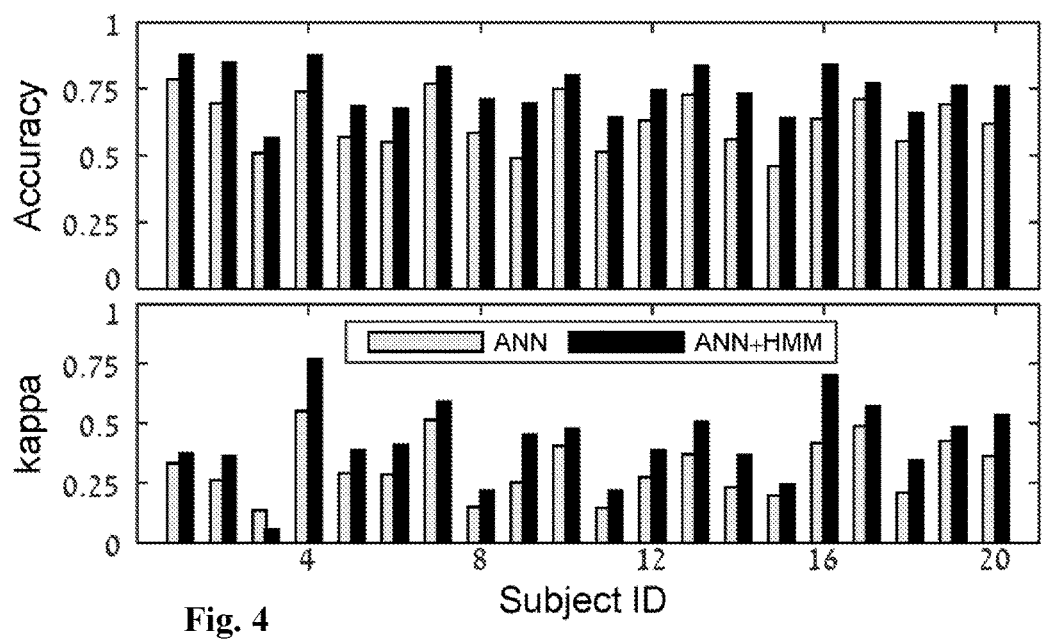
FIG. 4 shows the Epoch detection performance according to an embodiment of the present invention.

This study was performed on the database summarized in Table 1. For each subject, epoch-by-epoch MSS was compared between ABA and the PSG annotated sleep stages. The comparison was measured using simple agreement and using Cohen's kappa (shown in FIG. 4). FIG. 4 shows the Epoch detection performance. Upper panel—Subject epochs accuracy. Lower panel—Subject's epochs Cohen's kappa agreement. White bars represent epochs agreements based on ANN classification alone, and black bars represent the agreements after HMM procedure. The contribution of the time-series model (HMM) was also tested, presented as filled bars (FIG. 4). For the ANN model, the accuracy was 0.63±0.10 and kappa of 0.32±0.12. After applying the HMM, the performance was increased to 0.75±0.09 and 0.42±0.17. A confusion matrix is shown in Table 2.

TABLE 2

Classifiers confusion matrix.

| | | ANN Estimation | | | HMM Estimation | | |
|---|---|---|---|---|---|---|---|
| | | W | R | N | W | R | N |
| PSG annotation | W | 66% | 15% | 19% | 69% | 5% | 26% |
| | R | 8% | 64% | 28% | 5% | 54% | 41% |
| | N | 12% | 26% | 62% | 10% | 11% | 79% |

W—Wake, R—REM sleep, and N—NREM sleep. A priori probability for states are 14%, 12%, and 74% for Wake, REM, and NREM, respectively.

Figure 5:
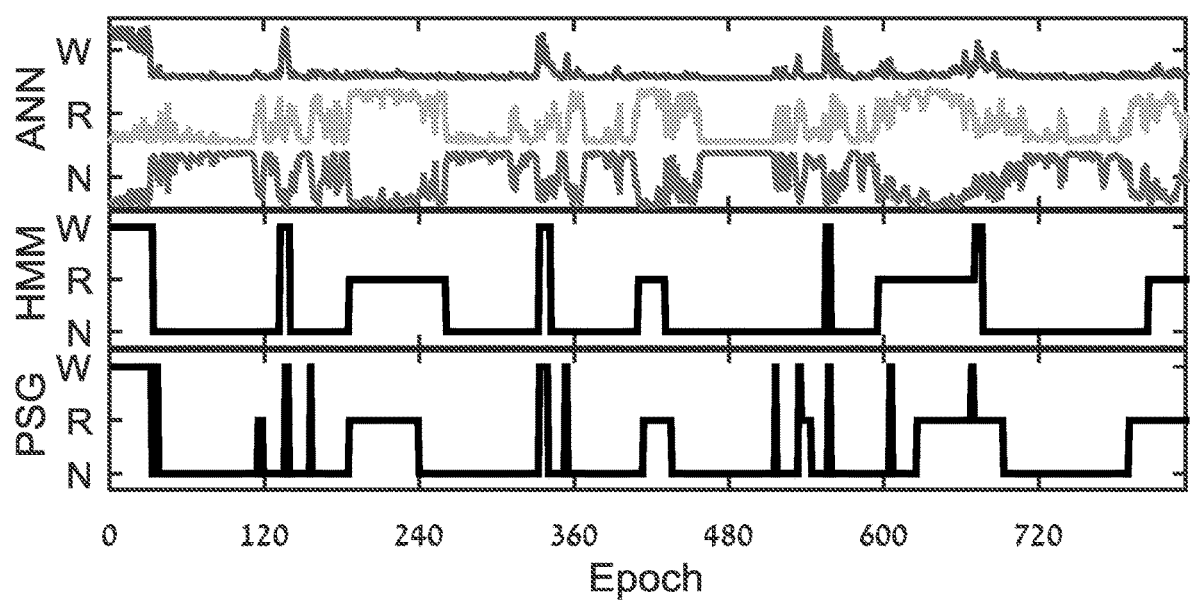
FIG. 5 presents a typical example of MSS estimation for a subject according to an embodiment of the present invention.

FIG. 5 presents a typical example of MSS estimation for a subject (ID #7 from FIG. 4). The upper panel presents the three classes MSS scores (probabilities) estimated by the ANN classifier (scores are summed to one). Center panel presents the HMM's most probable MSS sequence. Lower panel presents the PSG annotation. W-Wake, R-REM, N-NREM. Subject ID is #7 from FIG. 4: Male, age=44, BMI=28, AHI=11. This example exhibits an accuracy rate of 83% and kappa of 0.58.

Once MSS is estimated across the night, sleep quality parameters can be calculated. Table 3 shows the mean and SD values of the estimated sleep quality parameters for the validation study.

TABLE 3

Sleep Parameters For The Validation Dataset.

| Param. | PSG | ABA | ABA-PSG | Error | p |
|---|---|---|---|---|---|
| TST | 374 ± 38 | 358 ± 48 | −16 ± 47 | 36 ± 34 | .26 |
| (min) | 274-426 | 295-435 | −115-78 | 3-115 | |
| SL | 29 ± 28 | 33 ± 29 | 4 ± 27 | 17 ± 21 | .70 |

TABLE 3-continued

Sleep Parameters For The Validation Dataset.

| Param. | PSG | ABA | ABA-PSG | Error | p |
|---|---|---|---|---|---|
| (min) | 1-108 | 1-92 | −33-80 | 0-80 | |
| SE (%) | 92 ± 5<br>81-98 | 91 ± 7<br>73-100 | −1 ± 7<br>−20-14 | 5 ± 5<br>0-20 | .62 |
| WASO (min) | 30 ± 17<br>9-66 | 33 ± 29<br>0-114 | 3 ± 28<br>−46-86 | 20 ± 19<br>1-86 | .69 |
| AwI (#/hr) | 2.6 ± 1.1<br>0.6-5.7 | 0.6 ± 0.3<br>0.0-1.2 | −2.0 ± 1.2<br>−5.3--0.2 | 2.0 ± 1.2<br>0.2-5.3 | .00 |
| RL (min) | 185 ± 85<br>42-336 | 133 ± 63<br>32-253 | −45 ± 96<br>−271-83 | 77 ± 71<br>2-271 | .04 |
| RP (%) | 13 ± 6<br>4-25 | 17 ± 8<br>0-27 | 4 ± 8<br>−9-20 | 7 ± 5<br>0-20 | .09 |

TST—total sleep time, SL—sleep latency, SE—sleep efficiency, WASO—wake-time after sleep onset, AwI—awakening index, RL—REM latency, RP—REM percentage. Values are mean ± SD and range min-max. ABA—audio-based analysis, PSG—the gold standard polysomnography. Error defined as the absolute difference, and p represents the p-value of two-tail, paired t-test comparison. These analyses were based on 20 subjects from the validation dataset.

The demand for accessible sleep diagnosis and simple/easy to use PSG alternative is high. The performances of the present invention is very encouraging and could serve as a screening tool for MSS estimation using a simple single-channel, non-contact audio technology.

According to another aspect of the present invention, the sleep quality parameters relate to apnea, hypopnea and normal breathing events. Sleep-disordered breathing (SDB) is a group of common disorders that affect up to 20% of the population. Its prevalence has substantially increased over the past two decades: an increase of more than 14% in the North-American adult population. The most prominent disorder among this group is obstructive sleep apnea (OSA), which is characterized by recurrent events of partial or complete collapse of the upper airway during sleep (i.e., hypopnea and apnea). OSA can lead to excessive daytime sleepiness, cardiovascular morbidity, and death. Severity of OSA is measured by the apnea-hypopnea index (AHI), which is the average number of apnea and hypopnea events per hour of sleep.

While apnea is defined as a reduction of at least 90% in air flow for 10 seconds or more, hypopnea is characterized by a reduction of at least 30% in airflow that lasts 10 seconds or more, accompanied by 3% (or more) oxygen desaturation. The definition of hypopnea has been inconsistent since it was first termed and led to a significant variability of OSA severity estimations in different studies.

Few studies have attempted to determine the exact time location of apnea and hypopnea, and none of these studies distinguished between the two by non-contact acoustic sounds (e.g. A. H. Khandoker, J. Gubbi, and M. Palaniswami, "*Automated scoring of obstructive sleep apnea and hypopnea events using short-term electrocardiogram recordings,*" Information Technology in Biomedicine, IEEE Transactions on, vol. 13, pp. 1057-1067, 2009, and P. Várady, T. Micsik, S. Benedek, and Z. Benyó, "*A novel method for the detection of apnea and hypopnea events in respiration signals,*" Biomedical Engineering, IEEE Transactions on, vol. 49, pp. 936-942, 2002).

The present invention according to this aspect relates to a system and method for classification that can categorize and differentiate between complete respiratory obstruction sound (apnea), partial respiratory obstruction sound (hypopnea), and normal breathing events. This aspect is also based on recording sound of a user patient in a non-contact manner and based on analysis of acoustic features extracted from the audio signals recorded. This aspect according to the present invention is configured to calculate a Apnea-Hypopnea Index (AHI).

It should be noted that this aspect of the present invention is similar to the aspect of the MSS estimation mutatis mutandis. The following items are different. While in the MSS aspect the machine learning classifier is generated by using true result PSG annotated sleeping scores of each epoch being WAKE, REM and NREM, this SDB aspect of the present invention comprises alternatively using true result PSG annotated sleeping scores of each epoch being apnea, hypopnea and normal breathing. The whole machine learning process (classifier), the probability vectors, enhancing time series pattern function, calculating the most probable sleep quality parameters sequence, are all adapted mutatis mutandis. Other steps (e.g. pre-processing, breathing detection, feature extraction) are similar.

It should be noted that according to a specific embodiment the following features are particularly used with the SDB aspect: ADmean25, SuperSnore and XcorrPeak.

Figure 7:
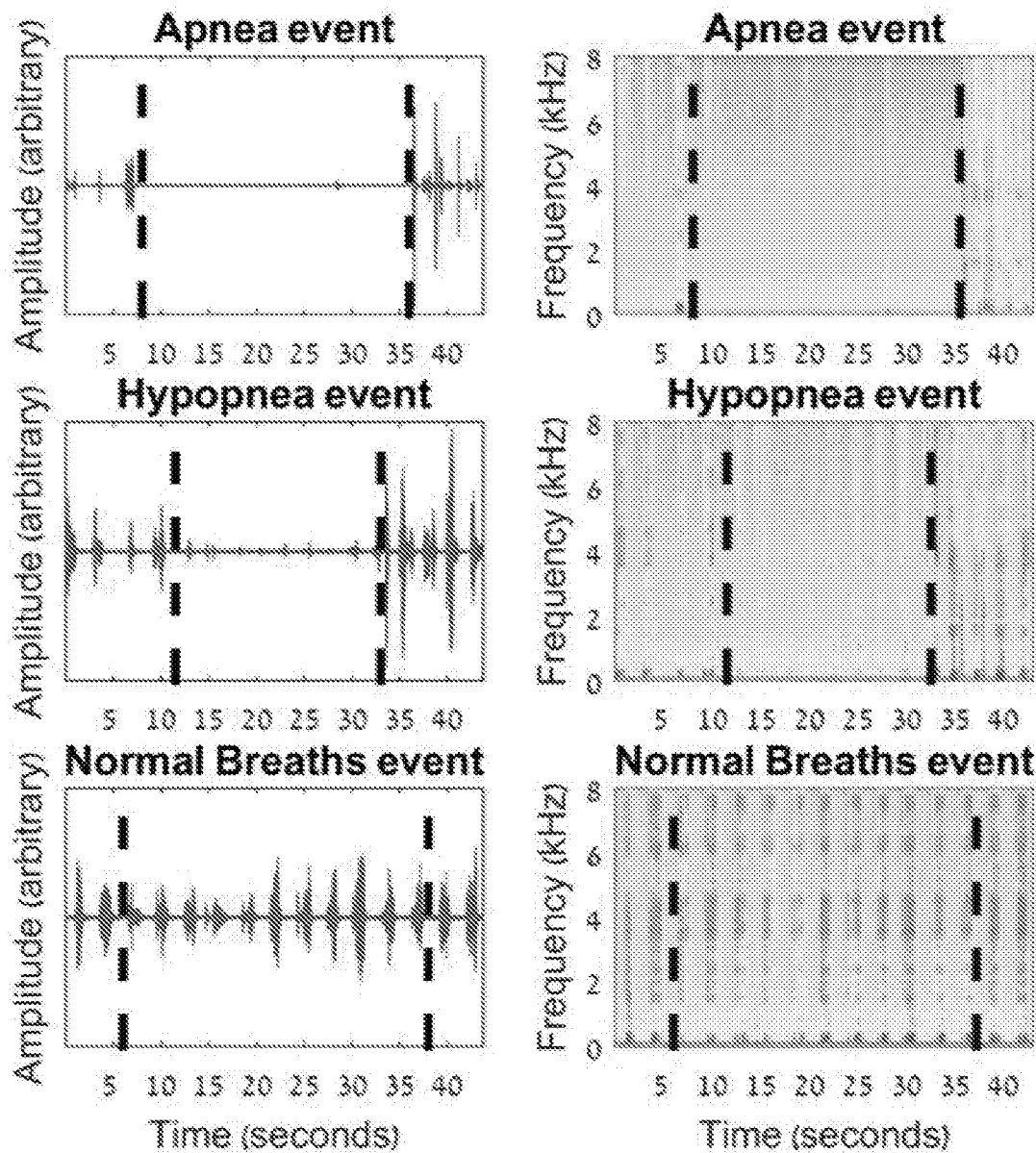
FIG. 7 shows examples of three different audio segments.

FIG. 7 shows examples of three different audio segments. Black dashed lines indicate events' beginning and ending.
  A) Apnea's amplitude in time (top left).
  B) Apnea's Frequency content in time (top right).
  C) Hypopnea's amplitude in time (middle left).
  D) Hypopnea's Frequency content in time (middle right).
  E) Normal Breath's amplitude in time (bottom left).
  F) Normal Breath's Frequency content in time (bottom right).

EXAMPLE 2

Figure 6A:
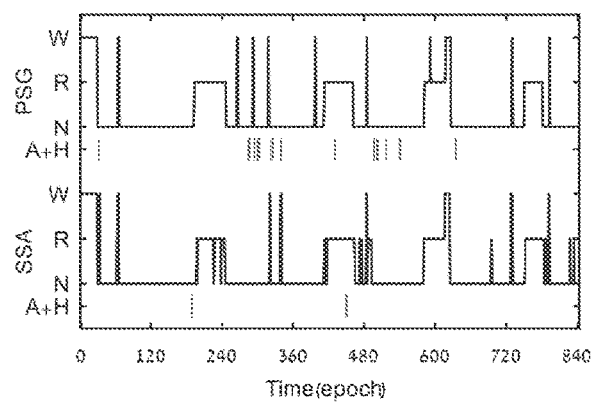
FIGS. 6A-6D show examples comparing macro sleep stages estimation between PSG and SSA (sleep sound analysis) in different cases.
Figure 6B:
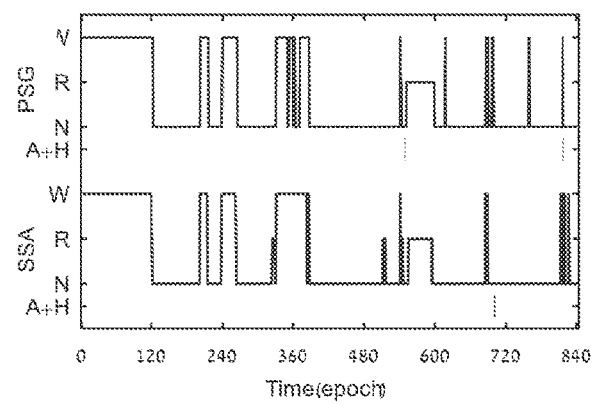
Figure 6C:
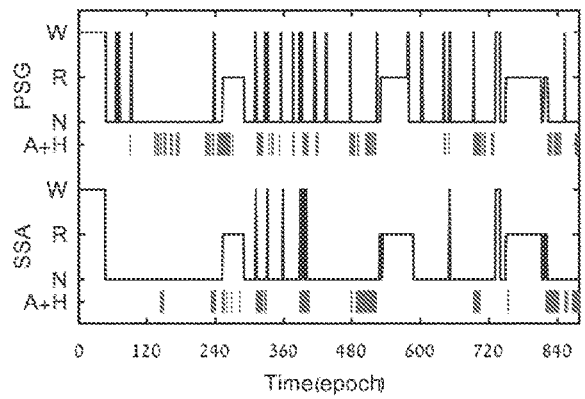
Figure 6D:
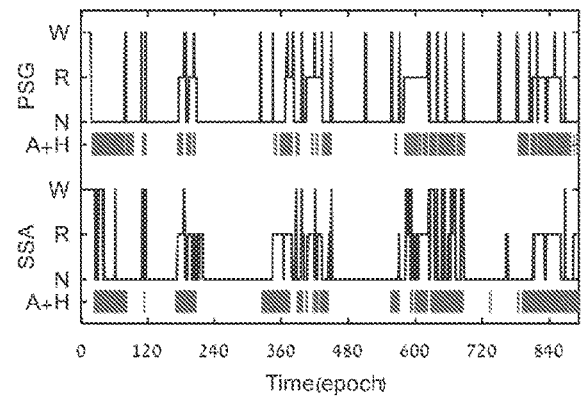

FIGS. 6A-6D show examples comparing macro sleep stages estimation between PSG and SSA (sleep sound analysis) in different cases.
  FIG. 6A) Healthy subject, apnea-hypopnea (A+H) index<5 (events per hour);
  FIG. 6B) Subject with long latency to rapid-eye-movement (R) sleep of about 440 epochs;
  FIG. 6C) Subject with moderate sleep apnea (A+H index=18 events per hour), note that obstructive events appear in both non-rapid-eye-movement (N), and in R sleep;
  FIG. 6D) R-related sleep apnea (A+H=55 events per hour in R, and 21 events per hour in N sleep).

In all cases very good agreement was found between polysomnography (PSG) and sleeping sound analysis (SSA) in estimating macro sleep stages (N, R, and W—wake) and detection of A+H.

EXAMPLE 3

In the current study, the acoustic characteristics of hypopnea in order to distinguish it from apnea was explored. The method—finding audio-based features that can discriminate between apnea, hypopnea and normal breathing events. Whole night audio recordings were performed using a non-contact microphone on 44 subjects, simultaneously with the polysomnography study (PSG). Recordings were segmented into 2015 apnea, hypopnea, and normal breath events and were divided to design and validation groups. A classification system was built using a 3-class cubic-kernelled support vector machine (SVM) classifier. Its input is a 36-dimensional audio-based feature vector that was extracted from each event. Three-class accuracy rate using the hold-out method was 84.7%. A two-class model to separate apneic events (apneas and hypopneas) from normal breath exhibited accuracy rate of 94.7%. Thus it is possible to detect apneas or hypopneas from whole night audio signals. This provides more insight about a patient's level of upper airway obstruction during sleep. This approach may be used for OSA severity screening and AHI estimation.

A classification system was proposed, aiming to categorize complete respiratory obstruction sound (apnea), partial respiratory obstruction sound (hypopnea), and normal breath events. The algorithm was designed and validated using the hold-out method. After the pre-processing procedure, a feature vector was extracted from each of the pre-segmented apnea, hypopnea, and normal breath events. As can be seen in FIG. 7, the three different event types have unique characteristics in both time and spectrum.

After passing a K-Best feature selection procedure, the resulting feature vector fed a cubic-SVM classifier that was designed to differentiate the three possible classes.

A. Experimental Setup

The database for this study includes 44 adult subjects (>18 years old) who were recorded during routine PSG study at the Sleep-Wake Disorders Unit, Soroka University Medical Center. Simultaneously with the PSG study, the subjects were recorded using a digital audio recording device (EDIROL R-4 Pro) connected to a non-contact directional condenser microphone (RØDE NTG-1) positioned one meter above the subjects' head. Subjects' characteristics are presented in Table 4.

TABLE 4

DATABASE DIVISION

| | No. of subjects | AHI [events/hr] (range) | BMI [kg/m$^2$] (range) | Age [yr] (range) |
|---|---|---|---|---|
| Design | 31 | 25.0 ± 19.1 (1.8-79.2) | 31.9 ± 4.4 (16.8-40.3) | 54.2 ± 12.9 (29.0-79.0) |
| Validation | 13 | 25.2 ± 21.1 (8.6-74.8) | 33.5 ± 6.2 (25.8-46.8) | 49.4 ± 12.3 (32.0-81.0) |

The values are presented as mean ± SD corresponding to the relevant units.

B. Segmentation

Whole-night recordings were analyzed epoch-by-epoch (30-second epochs) by a sleep expert. Segmentation was made into three different classes: apnea, hypopnea and normal breath events. Study design: 1578 events (674 apneas, 422 hypopneas, and 482 normal breaths). Study validation: 437 events (247 apneas, 58 hypopneas, and 132 normal breaths). Normal breath events were segmented in epochs that did not include apnea or hypopnea events.

C. Pre-Processing

Recorded audio signals were down-sampled from 44.1 to 16 kilohertz and an adaptive noise reduction algorithm, based on spectral subtraction, was applied.

D. Feature Extraction and Selection

For each apnea, hypopnea, and normal breath event, a 36-dimension feature vector was extracted. The feature vector includes features from both time and spectral domains, some of which are novel features developed in our lab. Features' capability of distinguishing the different classes (one feature at a time) was examined according to the meanAUC measure; a receiver operating characteristic (ROC) curve was formed for each 2-class combination, and area under the curve (AUC) was calculated. The meanAUC measure is the mean of these three AUCs received for each feature.

K-best feature selection process was applied over the different features, where its criterion was the meanAUC measure. K was selected so the best classification accuracy result was received for the training set.

Special Features Description

EX-ADmean25

During normal breathing segments, time signal amplitude varies significantly, in comparison to hypopnea events and apnea events, and its differentiation provides high values. This feature is computed as the mean of the higher quartile of the differentiation's absolute difference.

EX-SuperSnore

At the end of an apnea or a hypopnea event there might be a loud breath or snore that is supposed to compensate for the lack of oxygen caused by the cessation of breathing. This feature compares the maximal short-term energy (STE) in the 5-second window after the event terminates, with the maximal short-term energy during the event itself, and is computed as explained herein:

$$EX\text{-}SuperSnore = \frac{\max_{i=1,\ldots,N_a} STE_a(i)}{\max_{i=1,\ldots,N_a} STE_d(i)}$$

where $N_a$ resembles the number of time-frames in the after-event 5-second window, and $N_d$ resembles the number of time-frames during the event. $STE_a$ and $STE_d$ stand for the short−term energy sequences after the event and during the event, respectively.

High values are expected for the apnea events, whereas for normal breathing events the expected value is 1.

XcorrPeaksSTE

In the examination of 10-second time windows, the autocorrelation function of the short-term energy sequence among hypopnea and normal breath events tends to resemble a sine wave. Utilizing this tendency, XcorrPeaksSTE is computed using the coefficient of determination (R2) achieved from applying a 0.3 hertz sine wave curve fitting to the mentioned autocorrelation function.

EX-FCMDmean25

Breaths consist of high-frequency content, as can be seen in FIG. 7 (bottom right). Their existence in normal breath events and hypopnea events should expand the range of values of the frequency center of mass (FCM). Therefore, the mean of the higher quartile of the frequency center of mass time-derivative (FCMD) increases.

DutyCycle

Figure 9:
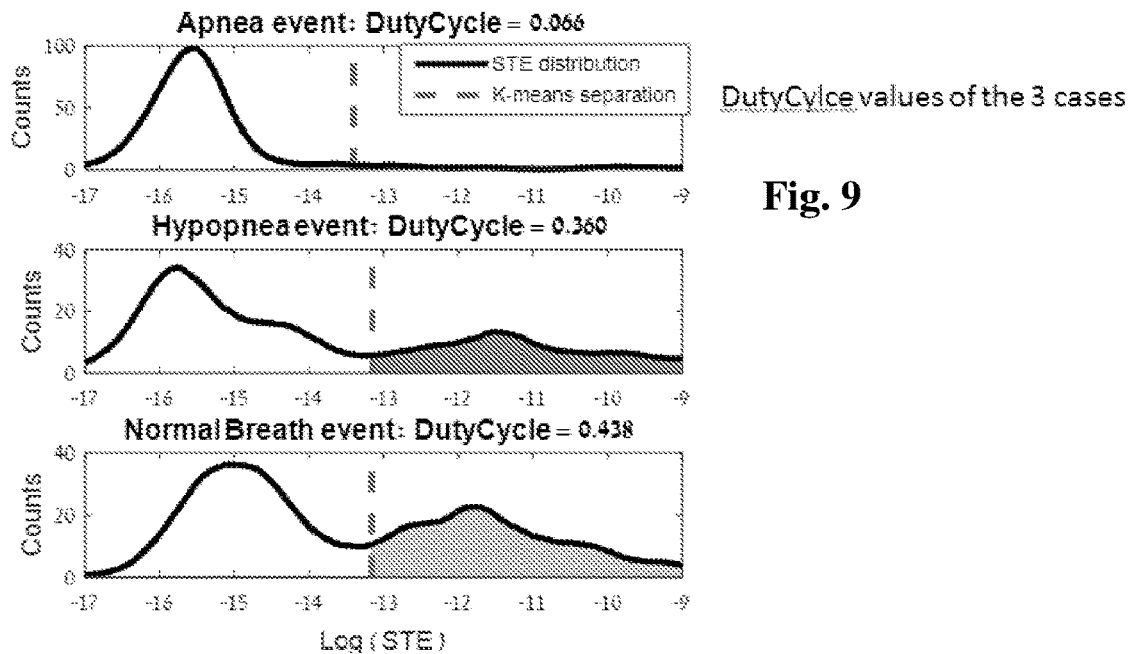
FIG. 9 shows an example of dutyCycle apnea, hypopnea and normal breathing events.

Each of the three classes discussed should provide a different distribution of the short-term energy values. This feature uses K-means algorithm (K=2) in order to separate higher energy content from lower energy content in the resulting STE histogram, as demonstrated in FIG. 9. The higher energy content and the lower energy content refer to breaths and background noise, respectively. DutyCycle is computed as the area of the higher energy content divided by the area of the entire energy content of the event. FIG. 9 shows an example of dutyCycle apnea, hypopnea and normal breathing events. FIG. 9 shows examples of the DutyCycle feature calculation for the 3 different event types. A) Apneas consist mostly of noise, therefore their DutyCycle value is low. B) Hypopneas include shallow breaths, hence higher STE values are obtained, which lead to higher DutyCycle outcomes compared to A. C) Normal breath events produce the highest DutyCycle values out of the three classes. It can be seen in FIG. 7 (bottom right) that indeed, the subject is breathing during almost half of the event.

Figure 10:
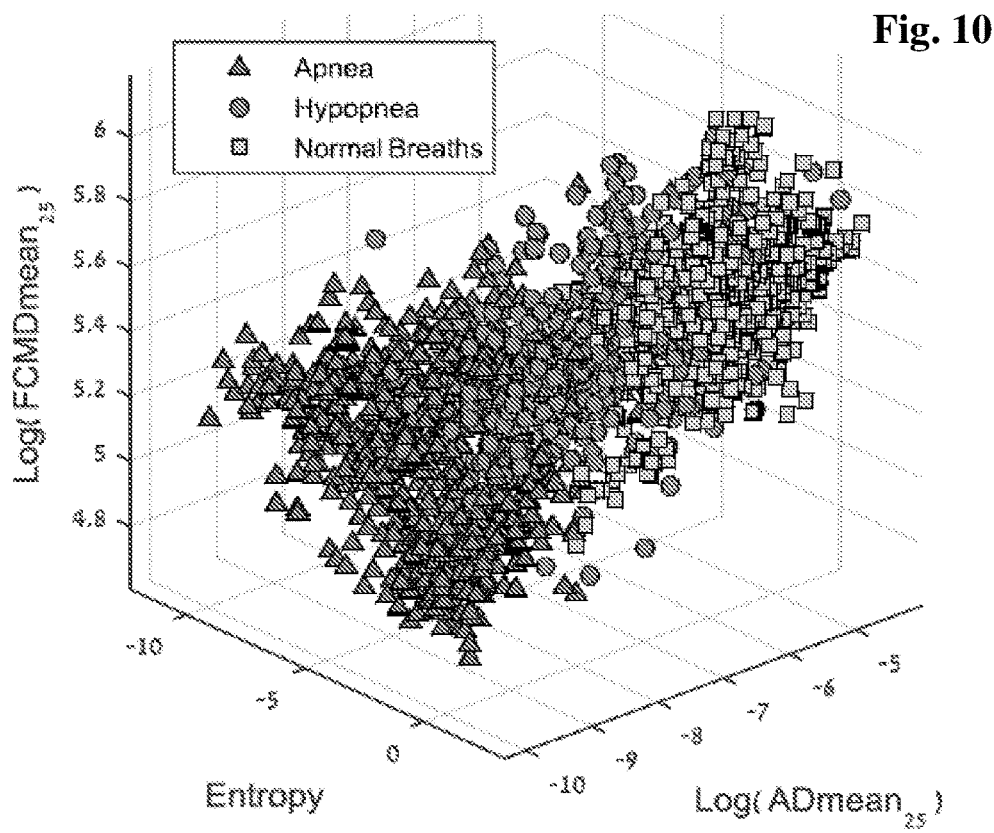
FIG. 10 shows an example of a 3-dimensional representation of one subset of three features.

FIG. 10 provides a 3-dimensional representation of one subset of three features out of the 36 extracted features. FIG. 10 provides Three-dimensional space representation of the entire database. A subset of three features is used to demonstrate the diverse scattering of the feature vectors among the three classes. One can see that most of the hypopnea events are located between the apnea and normal breath events.

E. Classification

In order to differentiate apnea, hypopnea, and normal breath sounds, a 3-class cubic-kernelled support vector machine (SVM) was designed and validated using the hold-out approach. As we are facing a 3-class classification problem, a multiclass method should be chosen for the binary SVM classifier; the One-vs-One method was selected, where one binary SVM learner is trained for each pair of classes. In addition, a second cubic SVM classifier was designed, distinguishing between two classes: apneic events (apneas and hypopneas together) and normal breath events. The latter classifier was also validated with the hold-out method, while the division of the data into design and validation groups remained.

The performance of the classifiers was evaluated using the accuracy measure, which is the number of events that were classified correctly divided by the total number of events.

Results and Discussion

Table 5 displays the meanAUCs that were calculated for 10 different features. According to these scores and using the design dataset, 27 features were selected in the K-best feature selection process out of the 36 possibilities. We noticed that many features from the time domain (e.g. Entropy, ADmean25 and STD) received high meanAUC scores.

TABLE 5

FEATURES' SCORE

| Feature Name | meanAUC |
| --- | --- |
| Entropy | 0.927 |
| Log(STEmean) | 0.924 |
| SuperSnore | 0.917 |
| ADmean$_{25}$ | 0.916 |
| STD | 0.910 |
| STEDmean$_{25}$ | 0.864 |
| FCMDmean$_{25}$ | 0.826 |
| XcorrFFT | 0.812 |
| DutyCycle | 0.793 |
| ZCR | 0.722 |

Using the hold-out method for validating the designed model, an accuracy rate of 84.7% was achieved for the 3-class classifier. Confusion matrix of the classifier's output is presented in Table 6. As expected, most of the errors were misclassification between hypopnea and the other two classes. This is because hypopnea is a sort of intermediate state between apnea and normal breaths; i.e. breaths exist, but are partially obstructed. This can be seen both in time and frequency domains, as demonstrated in FIG. 7. From the features aspect, FIGS. 9 and 10 also support this claim where hypopnea receives intermediate scores.

TABLE 6

3-CLASS CONFUSION MATRIX

| | Classification | | |
| --- | --- | --- | --- |
| True label | Apnea | Hypopnea | Normal Breath |
| Apnea (247) | 83.0% (205) | 15.0% (37) | 2.0% (5) |
| Hypopnea (58) | 12.0% (7) | 76.0% (44) | 12.0% (7) |
| Normal Breath (132) | 0.0% (0) | 8.4% (11) | 91.6% (121) |

The values in parentheses indicate absolute number of events.

TABLE 7

2-CLASS CONFUSION MATRIX

| | Classification | |
| --- | --- | --- |
| True label | Apneic event | Normal Breath |
| Apneic event (305) | 96.1% (293) | 3.9% (12) |
| Normal Breath (132) | 8.4% (11) | 91.6% (121) |

The values in parentheses indicate absolute number of events.

Clinically, in terms of AHI-directed evaluation of OSA severity, misclassification between apnea and hypopnea does not affect the resulting score. In FIG. 8 one can see the considerable overlap between apnea and hypopnea for the EX-SuperSnore feature (which is similar to the SuperSnore feature), which prevents a better separation of these two classes.

When designed and validated to distinguish between two classes (apneic events and normal breath events), the classifier achieved an accuracy of 93.4%. However, when diminishing the three classes problem into two classes, the model achieved better accuracy of 94.7%. This implies that even for the purpose of AHI assessment only, the separation between apnea and hypopnea contributes information. Confusion matrix of the 2-classes model's output is presented in Table 7 (above).

The AHI measure treats apnea and hypopnea in the same way when evaluating OSA severity, despite the fact that they are different by definition and by their acoustic features as well. Moreover, it takes as equal 15-second apnea and 60-second apnea, while the two might occur in separate sleep stages of a specific subject and probably indicate different OSA severity status.

While some of the embodiments of the invention have been described by way of illustration, it will be apparent that the invention can be carried into practice with many modifications, variations and adaptations, and with the use of numerous equivalents or alternative solutions that are within the scope of a person skilled in the art, without departing from the spirit of the invention, or the scope of the claims.

The invention claimed is:

1. A contactless method for determining levels of one or more gold standard sleep quality parameters based on audio analyses, the method comprising:
   using a microphone, acquiring and storing in memory an audio recorded signal comprising sleep sounds of a subject;
   segmenting the audio recorded signal, including at least audio originated from sounds of body movements and non-respiratory sounds, into epochs;

generating a feature vector for each epoch, wherein each of said feature vectors comprises one or more feature parameters that are associated with a particular characteristic of the audio recorded signal and that are calculated according to the epoch or according to a signal generated from the epoch;

inputting the generated feature vectors into a machine learning classifier and applying a preformed classifying model on the feature vectors that outputs a probabilities vector for each epoch, wherein each of the probabilities vectors comprises the probabilities of the epoch being each of macro sleep stages selected from the group consisting of WAKE, Rapid Eye Movement (REM), and Non-REM (NREM);

inputting the probabilities vectors for each epoch into a machine learning time series model and applying a preformed sleep quality time series pattern function on said probabilities vectors that outputs an enhanced probabilities vector for each epoch;

determining a final macro sleep stage for each epoch from said enhanced probabilities vectors; and utilizing said determined macro sleep stages, determining levels of gold standard sleep quality parameters including at least:
  a total sleep time (TST)—a sum of the durations of sleep states in a sleep period;
  a REM latency (RL)—a time span between a sleep onset and a first REM cycle, and
  a REM percentage (RP)—a ratio between a REM duration and the total sleep time (TST);wherein the one or more feature parameters are associated with characteristics of at least the sounds of body movements and non-respiratory sounds, in addition to characteristics selected from breathing sound content and breathing pattern periodicity;

wherein body movement sounds are determined from linen, pillow, and clothes rubbing and twitching; and wherein a determination of lack of body movement sounds is concluded as a REM state of the subject.

2. The method according to claim 1, further comprising carrying out a pre-processing stage comprising noise reduction from the audio recorded signal.

3. The method according to claim 1, further comprising carrying out a breathing detection stage comprising categorizing portions of the audio recorded signal as breathing and other portions of the audio recorded signal as non-breathing.

4. The method according to claim 1, wherein the one or more feature parameters comprise at least two feature parameters associated with at least two of the characteristics or comprise at least three feature parameters associated with at least three of the characteristics or comprise four feature parameters associated with the four characteristics.

5. The method according to claim 1, wherein the one or more feature parameters are all associated with one of the characteristics.

6. The method according to claim 5, wherein the one characteristic is breathing sound content.

7. The method according to claim 5, wherein the one characteristic is sounds of body movements.

8. The method according to claim 5, wherein the one characteristic is non-respiratory sounds.

9. The method according to claim 5, wherein the one characteristic is breathing pattern periodicity.

10. The method according to claim 1, wherein the one or more feature parameters associated with the breathing sound content characteristic are selected from the group consisting of Respiratory mean SNR feature, Respiratory Frequency centroid, ADmean25, SuperSnore, and XcorrPeak;

or wherein the one or more feature parameters associated with the body movements characteristic are selected from the group consisting of Body movement percentage feature and Body movement likelihood feature;

or wherein the one or more feature parameters associated with the non-respiratory sounds characteristic are selected from the group consisting of Non-breathing percentage feature, Non-breathing 90% SNR feature and Non-breathing frequency centroid feature;

or wherein the one or more feature parameters associated with the breathing pattern periodicity characteristic are selected from the group consisting of Respiratory cycle duty feature, respiratory cycle period feature, respiratory cycle intensity feature and respiratory cycle consistency feature.

11. The method according to claim 1, wherein the one or more feature parameters are each selected from the group consisting of respiratory cycle duty feature, respiratory cycle period feature, respiratory cycle intensity feature, respiratory cycle consistency feature, non-breathing percentage feature, respiratory mean SNR feature, respiratory frequency centroid feature, non-breathing 90% SNR feature, non-breathing frequency centroid feature, ADmean25, SuperSnore and XcorrPeak.

12. The method according to claim 1, further comprising a training stage of generating the preformed classifying model comprising:
  obtaining training audio recorded signals comprising sleep sounds of a plurality of subjects;
  segmenting the training audio recorded signals into corresponding training epochs;
  generating a training feature vector for each training epoch,
  wherein each of said training feature vectors comprises one or more training feature parameters that are associated with a particular characteristic of the training epoch and that are calculated according to the training epoch or according to a training signal generated from the training epoch;
  inputting the generated training feature vectors of each subject into training machine learning classifier along with corresponding true result annotated sleeping scores; and
  generating the preformed classifying model according to said training machine learning classifier.

13. The method according to claim 1, wherein the preformed sleep quality time series pattern function is generated by at least:
  inputting into a training machine learning model a plurality of true result hypnograms divided into training epochs, wherein each hypnogram comprises a macro sleep stage result for each of its training epochs; and
  applying a training machine learning on said plurality of true result hypnograms taking into account epoch time sequences, and macro sleep stages at each epoch time sequence.

14. The method according to claim 1, wherein calculating the most probable macro sleep stage sequence is carried out by using Viterbi algorithm.

15. The method according to claim 1, further comprising an initial step of recording the audio signal.

16. The method according to claim 1, wherein the macro sleep stages are sleep-disordered breathing parameters selected from the group consisting of apnea, hypopnea, and normal breathing.

17. The method of claim 1, wherein the macro sleep stages are further utilized to determine levels of the following gold standard sleep quality parameters:
- a sleep latency (SL)—an elapsed time to falling asleep from a time of lying down to go to sleep;
- a sleep efficiency (SE)—a ratio between TST and total time spent lying down to sleep during the sleep period;
- a wake-time after sleep onset (WASO)—a sum of the durations of awake states during the sleep period; and
- an awakening index (AI)—equal to an average number of times per hour a person awakes from sleep during the sleep period.

18. A contactless system for determining levels of one or more gold standard sleep quality parameters based on audio analyses, comprising:
- a processor;
- a memory coupled to the processor and configured to store program instructions executable by the processor to implement operations for determining macro sleep stages according to audio analyses, comprising:
    - using a microphone, acquiring and storing in the memory an audio recorded signal comprising sleep sounds of a subject;
    - segmenting into epochs the recorded signal, including at least audio originated from sounds of body movements and non-respiratory sounds;
    - generating a feature vector for each epoch,
    - wherein each of said feature vectors comprises one or more feature parameters that are associated with a particular characteristic of the signal and that are calculated according to the epoch or according to a signal generated from the epoch;
    - inputting the generated feature vectors into a machine learning classifier and applying a preformed classifying model on the feature vectors that outputs a probabilities vector for each epoch, wherein each of the probabilities vectors comprises the probabilities of the epoch being each of macro sleep stages selected from the group consisting of WAKE, REM, and NREM;
    - inputting the probabilities vectors for each epoch into a machine learning time series model and applying a preformed sleep quality time series pattern function on said probabilities vectors that outputs an enhanced probabilities vector for each epoch;
    - determining a final macro sleep stage for each epoch from said enhanced probabilities vectors; and
    - utilizing said determined macro sleep stages, determining levels of gold standard sleep quality parameters including at least:
        - a total sleep time (TST)—a sum of the durations of sleep states in a sleep period;
        - a REM latency (RL)—a time span between a sleep onset and a first REM cycle, and
        - a REM percentage (RP)—a ratio between a REM duration and the total sleep time (TST);wherein the one or more feature parameters are associated with characteristics of at least the sounds of body movements and non-respiratory sounds, in addition to characteristics selected from breathing sound content and breathing pattern periodicity;
    - wherein body movement sounds are determined from linen, pillow, and clothes rubbing and twitching; and
    - wherein a determination of lack of body movement sounds is concluded as a REM state of the subject.

19. The system of claim 18, wherein the macro sleep stages are further utilized to determine levels of the following gold standard sleep quality parameters:
- a sleep latency (SL)—an elapsed time to falling asleep from a time of lying down to go to sleep;
- a sleep efficiency (SE)—a ratio between TST and total time spent lying down to sleep during the sleep period;
- a wake-time after sleep onset (WASO)—a sum of the durations of awake states during the sleep period; and
- an awakening index (AI)—equal to an average number of times per hour a person awakes from sleep during the sleep period.

20. A contactless method for determining levels of one or more gold standard sleep quality parameters according to audio analyses, the method comprising:
- using a microphone, acquiring and storing in memory an audio recorded signal comprising sleep sounds of a subject;
- segmenting the audio signal, including at least audio originated from sounds of body movements and non-respiratory sounds, into epochs;
- generating a feature vector for each epoch,
- wherein each of said feature vectors comprises one or more feature parameters that are associated with a particular characteristic of the audio recorded signal and that are calculated according to the epoch or according to a signal generated from the epoch;
- inputting the generated feature vectors into a machine learning classifier and applying a preformed classifying model on the feature vectors that outputs a probabilities vector for each epoch, wherein each of the probabilities vectors comprises the probabilities of the epoch being each macro sleep stages selected from the group consisting of WAKE, Rapid Eye Movement (REM), and Non-REM (NREM);
- determining from said probability vectors a final macro sleep stage for each epoch; and
- utilizing said determined macro sleep stages, determining levels of gold standard sleep quality parameters including at least:
    - a total sleep time (TST)—a sum of the durations of sleep states in a sleep period;
    - a REM latency (RL)—a time span between a sleep onset and a first REM cycle, and
    - a REM percentage (RP)—a ratio between a REM duration and the total sleep time (TST);wherein the one or more feature parameters are associated with characteristics of at least the sounds of body movements and non-respiratory sounds, in addition to characteristics selected from breathing sound content and breathing pattern periodicity;
- wherein body movement sounds are determined from linen, pillow, and clothes rubbing and twitching; and
- wherein a determination of lack of body movement sounds is concluded as a REM state of the subject.

21. The method of claim 20, wherein the macro sleep stages are further utilized to determine levels of the following gold standard sleep quality parameters:
- a sleep latency (SL)—an elapsed time to falling asleep from a time of lying down to go to sleep;
- a sleep efficiency (SE)—a ratio between TST and total time spent lying down to sleep during the sleep period;
- a wake-time after sleep onset (WASO)—a sum of the durations of awake states during the sleep period; and an awakening index (AI)—equal to an average number of times per hour a person awakes from sleep during the sleep period.

* * * * *